United States Patent
Ito et al.

(10) Patent No.: US 10,448,826 B2
(45) Date of Patent: Oct. 22, 2019

(54) VISUAL FUNCTION TESTING DEVICE AND VISUAL FUNCTION TESTING SYSTEM

(71) Applicant: KABUSHIKI KAISHA TOPCON, Itabashi-ku (JP)

(72) Inventors: Ryosuke Ito, Itabashi-ku (JP); Hitoshi Shimizu, Itabashi-ku (JP); Kenji Miyashita, Okegawa (JP)

(73) Assignee: KABUSHIKI KAISHA TOPCON, Tokyo (JP)

( * ) Notice: Subject to any disclaimer, the term of this patent is extended or adjusted under 35 U.S.C. 154(b) by 264 days.

(21) Appl. No.: 15/326,315

(22) PCT Filed: Jun. 5, 2015

(86) PCT No.: PCT/JP2015/066332
§ 371 (c)(1),
(2) Date: Apr. 12, 2017

(87) PCT Pub. No.: WO2016/009739
PCT Pub. Date: Jan. 21, 2016

(65) Prior Publication Data
US 2017/0209044 A1 Jul. 27, 2017

(30) Foreign Application Priority Data
Jul. 18, 2014 (JP) .................................. 2014-147978

(51) Int. Cl.
*A61B 3/08* (2006.01)
*A61B 3/12* (2006.01)
(Continued)

(52) U.S. Cl.
CPC .......... *A61B 3/1225* (2013.01); *A61B 3/0025* (2013.01); *A61B 3/0091* (2013.01);
(Continued)

(58) Field of Classification Search
CPC ..... A61B 3/0025; A61B 3/0091; A61B 3/005; A61B 3/024; A61B 3/028; A61B 3/032;
(Continued)

(56) References Cited

U.S. PATENT DOCUMENTS

2006/0087618 A1   4/2006   Smart et al.
2010/0249532 A1   9/2010   Maddess et al.
(Continued)

FOREIGN PATENT DOCUMENTS

JP    7-303609 A    11/1995
JP    11-267101 A   10/1999
(Continued)

OTHER PUBLICATIONS

International Search Report dated Sep. 1, 2015, in PCT/JP2015/066332 filed Jun. 5, 2015.

*Primary Examiner* — Mustak Choudhury
(74) *Attorney, Agent, or Firm* — Xsensus LLP

(57) ABSTRACT

The objects of an embodiment are to improve the reliability of visual function examination and to shorten the time required for the examination. A visual function examination apparatus of an embodiment includes an application optical system, a biological information detector, and an evaluation information generator. The application optical system includes an optical scanner disposed in an optical path of laser light output from a laser light source, and is configured to apply the laser light that has travelled via the optical scanner to a retina of a subject's eye. The biological information detector is configured to detect biological information representing a reaction of a subject to application of the laser light. The evaluation information generator is configured to generate evaluation information on visual function of the subject's eye based on the biological information detected.

20 Claims, 26 Drawing Sheets

(51) Int. Cl.
  *A61B 3/00* (2006.01)
  *A61B 3/113* (2006.01)
  *A61B 3/18* (2006.01)

(52) U.S. Cl.
  CPC .............. *A61B 3/113* (2013.01); *A61B 3/18* (2013.01); *A61B 2503/08* (2013.01)

(58) Field of Classification Search
  CPC ......... A61B 3/08; A61B 3/10–12; A61B 3/15; A61B 3/18; A61B 3/113; A61B 3/152; A61B 3/1025; A61B 3/1225; A61B 5/04842; G02B 27/0172; G02B 27/0176
  USPC ....... 351/201, 205, 208, 209, 221, 222, 246, 351/206; 345/8; 600/300
  See application file for complete search history.

(56) References Cited

U.S. PATENT DOCUMENTS

| | | |
|---|---|---|
| 2012/0062842 A1 | 3/2012 | Griggio et al. |
| 2012/0113390 A1 | 5/2012 | Torii et al. |
| 2012/0188623 A1* | 7/2012 | Inoue .................. G02B 26/101 359/197.1 |
| 2013/0044042 A1 | 2/2013 | Olsson et al. |
| 2014/0028976 A1 | 1/2014 | Tanassi et al. |
| 2014/0036230 A1 | 2/2014 | Nef et al. |
| 2015/0103316 A1 | 4/2015 | Torii et al. |

FOREIGN PATENT DOCUMENTS

| | | | |
|---|---|---|---|
| JP | 2004-216118 A | | 8/2004 |
| JP | 2004216118 A | * | 8/2004 |
| JP | 2005-524432 A | | 8/2005 |
| JP | 2009-268778 A | | 11/2009 |
| JP | 2011-502590 A | | 1/2011 |
| JP | 2012-100713 A | | 5/2012 |
| JP | 2012-155019 A | | 8/2012 |
| JP | 2012-522569 A | | 9/2012 |
| JP | 2014-23768 A | | 2/2014 |
| JP | 2014-36844 A | | 2/2014 |
| JP | 2014-104174 A | | 6/2014 |
| WO | WO 2006/106877 A1 | | 10/2006 |

* cited by examiner

FIG. 10A

| LAYER THICKNESS d | INITIAL INTENSITY |
|---|---|
| $0 \leq d < d_1$ | $B_1$ |
| $d_1 \leq d < d_2$ | $B_2$ |
| $d_2 \leq d < d_3$ | $B_3$ |
| ..... | ..... |
| $d_i \leq d < d_{(i+1)}$ | $B_{(i+1)}$ |
| ..... | ..... |
| $d_{(n-1)} \leq d$ | $B_n$ |

VISUAL FUNCTION TESTING DEVICE AND VISUAL FUNCTION TESTING SYSTEM

FIELD

Embodiments described herein relate generally to an apparatus and a system used for examining visual functions.

BACKGROUND

The visual function is a complex sensory function by the optical system, the nervous system and the brain. The optical system includes the cornea, the crystalline lens, the pupil (iris), and the like, and performs adjustment of light amount, focus adjustment, and the like. The nervous system includes the retina, the visual pathways, and the like. Photoreceptor cells are arrayed in the retina. The photoreceptor cells convert an image formed by the optical system on the retina (light intensity, wavelength distribution, and the like) into nervous signals. The nervous signals are transmitted to the brain through visual pathways, and processed by the brain.

Visual field examination (or perimetry) is a typical example of the visual function examination. The visual field examination includes static visual field examination and dynamic visual field examination. In the static visual field examination, a photic stimulus (spot light, etc.) whose size is constant and whose intensity (brightness) is variable is projected to a specific position on the retina. The examinee pushes a button when having visually recognized the photic stimulus. Through sequential performance of this process for a plurality of positions of the retina, sensitivity for each site of the retina (that is, sensitivity distribution) can be obtained. In the dynamic visual field examination, the projection position of a photic stimulus onto the retina is moved. The examinee pushes a button when having visually recognized the photic stimulus. Thereby, a range visible by the subject's eye (that is, a shape of the visual field of the subject's eye) is obtained.

Another typical examination is flicker perimetry. In the flicker perimetry, a photic stimulus whose flicker frequency (frequency of brightness change) is variable is presented to the subject's eye, and a threshold value of the flicker frequency recognizable by the subject is obtained.

Patent Document 1: Japanese Unexamined Patent Publication No. 2014-36844

Patent Document 2: Japanese Unexamined Patent Publication No. 11-267101

As described above, the visual function examination is performed based on the subject's responses to photic stimuli. Therefore, when the subject is unfamiliar with the examination or is an elderly person, the subject may make mistakes with his/her response or he/she may provide a delayed response, leading to problems such as decreasing reliability of the examination and prolongation of the examination. Considering that the time required for a visual function examination is relatively long in general (for example, about several tens of minutes), prolongation of the examination reduces the concentration of the subjects and causes a further decrease in reliability of the examination as well as is putting the examiner under a great deal of strain.

SUMMARY

The present invention is for solving aforementioned problems, and the object thereof is to improve the reliability of the visual function examination and to shorten the time required for the visual function examination.

A visual function examination apparatus according to an embodiment includes: an application optical system including an optical scanner disposed in an optical path of laser light output from a laser light source and configured to apply the laser light that has travelled via the optical scanner to a retina of a subject's eye; a biological information detector configured to detect biological information representing a reaction of a subject to application of the laser light; and an evaluation information generator configured to generate evaluation information on visual function of the subject's eye based on the biological information detected.

According to the embodiments, it is possible to improve the reliability of the visual function examination and to shorten the time required for the visual function examination.

BRIEF DESCRIPTION OF THE DRAWINGS

FIG. 10A is a schematic diagram illustrating an example of the configuration of the visual function examination apparatus according to a modification.

DETAILED DESCRIPTION

Embodiments of the present invention are described below. The apparatus and the systems according to the embodiments are used for a visual function examination. The embodiments may be configured to be able to perform arbitrary kinds of visual function examinations. The embodiments are configured to be able to perform either any one of or both of static visual field examination and dynamic visual field examination, for example.

According to the embodiments, the visual function examination that can be performed includes a step of applying a photic stimulus to a retina with laser light, a step of detecting a reaction of the subject to the photic stimulus, and a step of evaluating the visual function based on the reaction detected. In the step of detecting the reaction of the subject, biological information of the subject is detected. The biological information may be arbitrary information that varies with photic stimulation. Examples of methods for acquiring the biological information include an electroencephalography, an electroretinography, a magnetoencephalography, a brain measurement with optical topography, a functional MRI, a pupil diameter measurement, and the like. In the embodiments, one or more types of biological information are acquired. The forms of the evaluation information acquired through the visual function examination according to the embodiments may be different according to the types of examinations.

Hereinafter, some typical embodiments and modifications will be described, but the present invention is not limited thereto. In addition, two or more of these embodiments and modifications can be combined in arbitrarily ways.

First Embodiment

Figure 1:
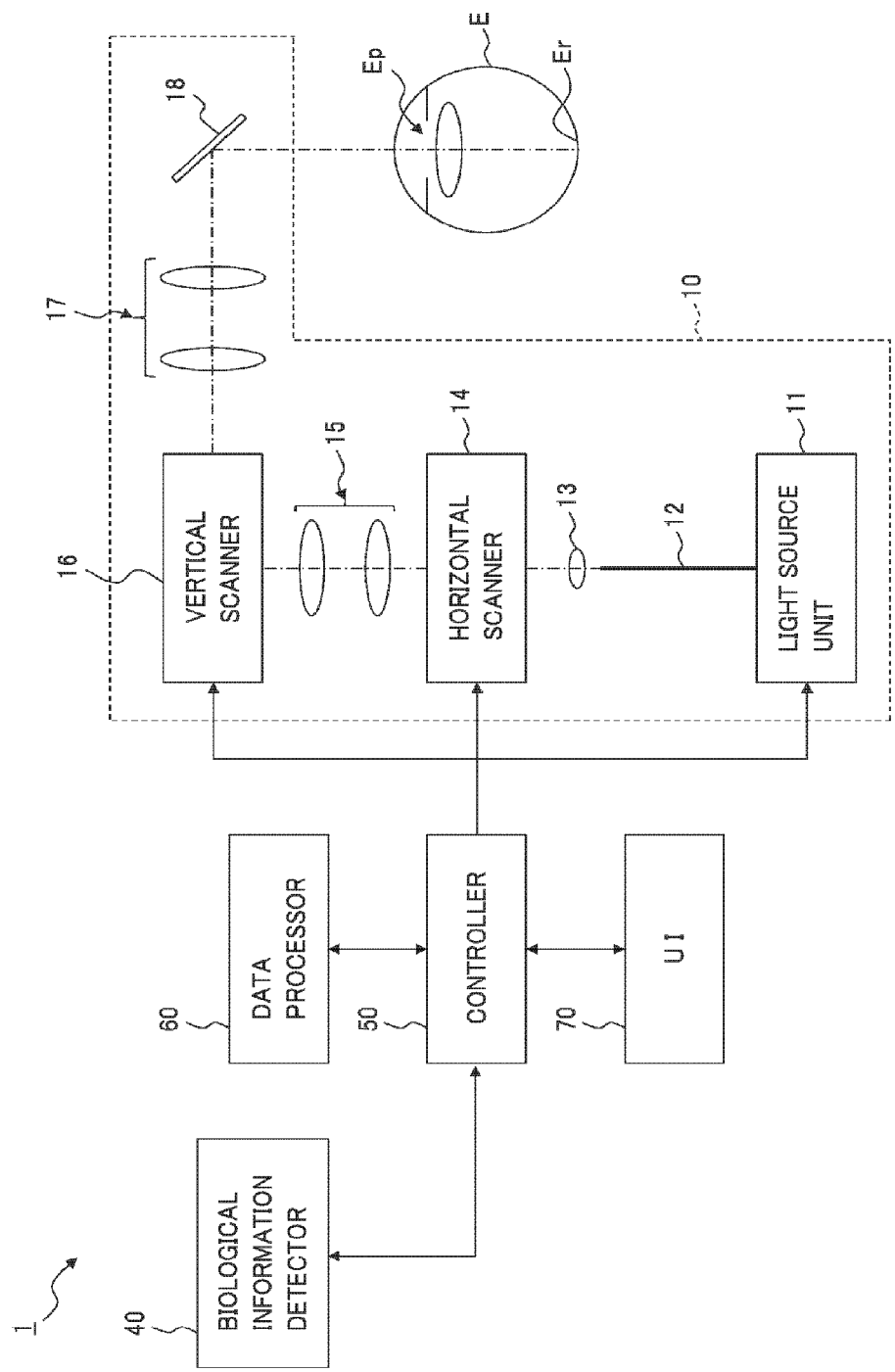
FIG. 1 is a schematic diagram illustrating an example of the configuration of a visual function examination apparatus according to an embodiment.
Figure 2:
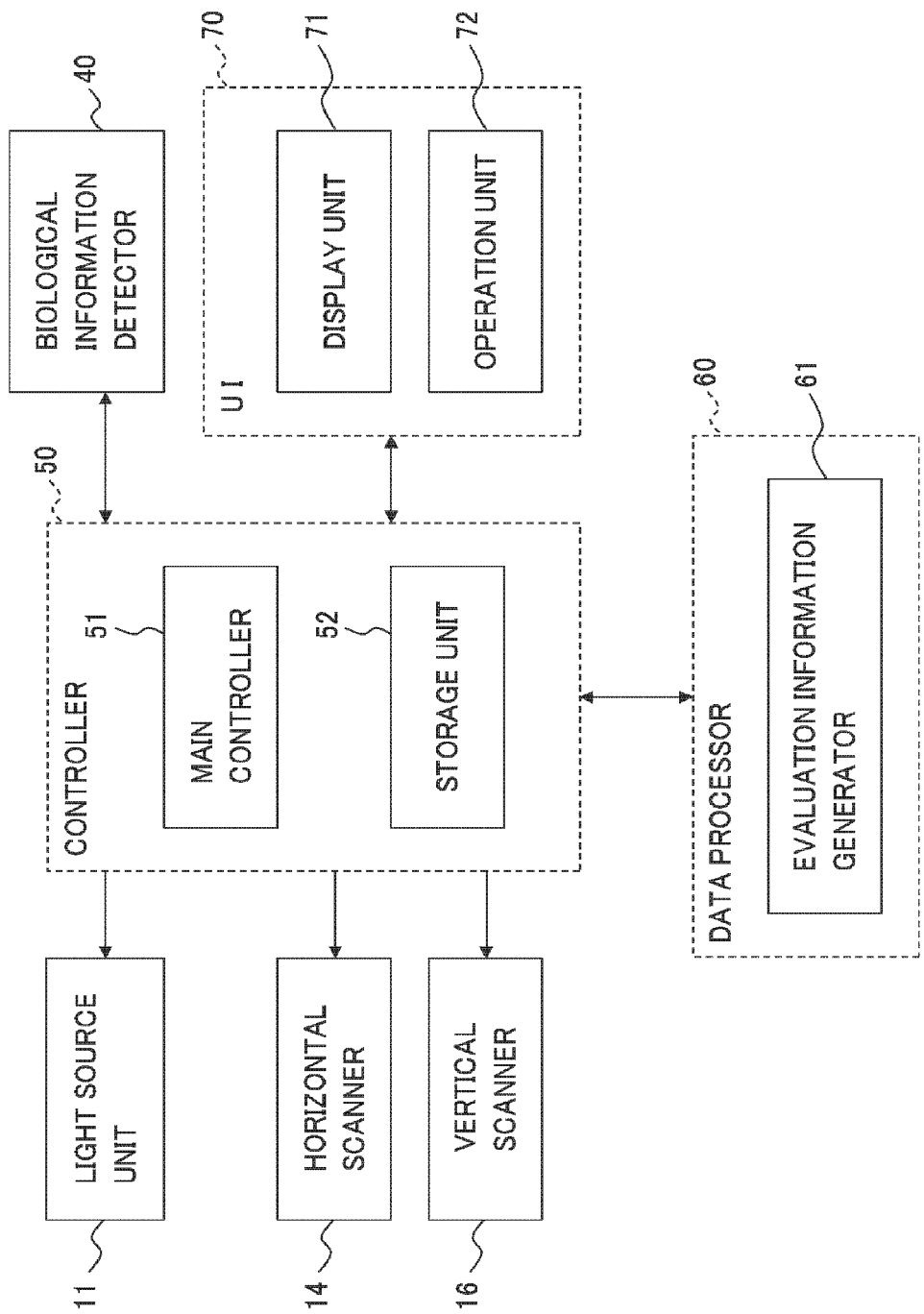
FIG. 2 is a schematic diagram illustrating an example of the configuration of the visual function examination apparatus according to the embodiment.

The visual function examination apparatus 1 shown in FIG. 1 is used for examining the visual function of the subject's eye E. The visual function examination apparatus 1 includes an application optical system 10, a biological information detector 40, a controller 50, a data processor 60, and a user interface (UI) 70. FIG. 2 shows an example of the configuration of the controller 50, the data processor 60, and the user interface 70.

(Application Optical System 10)

The application optical system 10 includes an optical system for presenting information (for example, for applying photic stimulus) to the subject's eye by scanning the retina with laser light. The application optical system 10 functions as a retinal scanning display which is an example of a scanning type image display apparatus. The retinal scanning display is a known technology and is disclosed in, for example, Japanese Unexamined Patent Application Publication No. 2012-155019 and US Patent Publication No. 2013/0044042. FIG. 1 shows an outline of the configuration of the application optical system 10. The application optical system 10 may further include one or more components disclosed in the above-mentioned publications or the like.

The application optical system 10, of which an outline is shown in FIG. 1, includes a light source unit 11, an optical fiber 12, a collimating optical system 13, a horizontal scanner 14, a relay optical system 15, a vertical scanner 16, a relay optical system 17 and a reflecting mirror 18.

The light source unit 11 outputs laser light. Although not shown, the light source unit 11 includes one or more laser light sources, one or more laser drivers for driving the laser light sources, and a circuit for supplying a drive signal to the laser drivers. The laser light source outputs visible laser light. In the case where the light source unit 11 includes two or more laser light sources, these laser light sources may be configured to be capable of outputting different types of laser light from one another. The types of the laser light include types related to wavelength bands (colors), types related to intensity (light quantity), and the like.

Further, the light source unit 11 includes a collimating optical system (not shown) for collimating laser light output from each laser light source into a parallel light beam. In the case where the light source unit 11 includes two or more laser light sources, the light source unit 11 may include a combining optical system (not shown) that combines two or more optical paths respectively extending from the two or more laser light sources into one. The combining optical system includes, for example, a dichroic mirror and/or a half mirror. The single optical path formed by combining the optical paths with the combining optical system is led to one end of the optical fiber 12 via a condensing optical system (not shown).

The light source unit 11 outputs one or more types of laser light in the way described above. The laser light output from the light source unit 11 is guided by the optical fiber 12, and is emitted from the optical fiber 12. The laser light emitted from the fiber end is collimated into a parallel light beam by the collimating optical system 13, and then enters the horizontal scanner 14.

The horizontal scanner 14 deflects the laser light in the horizontal direction. That is, the horizontal scanner 14 generates a horizontal scan of the laser light. The horizontal scanner 14 includes an arbitrary type of single-axis deflecting mirror such as a galvano mirror, a resonant mirror, a MEMS (Micro Electro Mechanical Systems) mirror, a polygon mirror, or the like. The laser light that has travelled via the horizontal scanner 14 is guided to the relay optical system 15.

The relay optical system 15 relays the laser light between the horizontal scanner 14 and the vertical scanner 16. The relay optical system 15 includes, for example, two or more lenses having positive refractive power. The laser light having passed through the relay optical system 15 enters the vertical scanner 16.

The vertical scanner 16 deflects the laser light in the vertical direction. That is, the vertical scanner 16 generates a vertical scan of the laser light. The vertical scanner 16 includes an arbitrary type of single-axis deflecting mirror such as a galvano mirror, a resonant mirror, a MEMS mirror, a polygon mirror, or the like. The laser light that has travelled via the vertical scanner 16 is guided to the relay optical system 17.

The relay optical system 17 relays the laser light between the vertical scanner 16 and the reflecting mirror 18. The relay optical system 17 includes, for example, two or more lenses having positive refractive power. The laser light having passed through the relay optical system 17 is reflected toward the subject's eye E by the reflecting mirror 18. The laser light incident on the subject's eye E passes through the pupil Ep and is projected onto the retina Er.

Here, the horizontal scan and the vertical scan will be described. In the example shown in FIG. 1, it is assumed that the subject's eye E is shown as a top view. In this case, the application optical system 10 is arranged on the left side of the subject's eye E, and the subject's eye E corresponds to the left eye of the subject. In such an assumption, "horizontal direction" corresponds to a direction along the paper surface of FIG. 1 (lateral direction), and "vertical direction" perpendicular to the "horizontal direction" corresponds to a direction perpendicular to the paper surface of FIG. 1. Such combination of the horizontal scanner 14 and the vertical scanner 16 makes it possible to carry out two-dimensional scanning of the retina Er of the subject's eye E with the laser light.

Note that in the example shown in FIG. 1, the horizontal scanner 14 is disposed on the upstream side (that is, on the side of the light source unit 11), and the vertical scanner 16 is disposed on the downstream side (that is, the subject's eye E side); however, the configuration for generating the two-dimensional scanning is not limited to this. For example, a configuration may be employed in which the vertical scanner is arranged on the upstream side of the horizontal scanner. Further, the horizontal scanner and the vertical scanner may be a single optical scanner. In that case, for example, a single optical scanner equipped with a two-axis deflecting mirror is employed.

(Biological Information Detector 40)

The biological information detector 40 detects biological information representing the reaction of the subject to the application of the laser light to the retina Er. As described above, the biological information is an arbitrary type of information that changes according to photic stimulation. Further, the biological information detector 40 may be configured to acquire two or more types of biological information.

Examples of the biological information include an electroencephalogram, an electroretinogram, a magnetoencephalogram, an optical topogram of the brain, a functional MRI image, a pupil diameter, and the like. Various kinds of biological information including these are acquired by known methods (with known devices) corresponding to the type. The biological information detector 40 includes a device(s) for acquiring one or more of various kinds of biological information. For example, the biological information detector 40 includes an electroencephalograph, an electroretinograph, a magnetoencephalograph, an optical topograph, an MRI apparatus, an anterior segment imaging camera, and the like. It should be noted that the anterior segment imaging camera is used for imaging the anterior segment of the subject's eye E from the front. Analyzing the anterior segment image acquired by the anterior segment imaging camera provides the size (for example, diameter) of the pupil Ep.

(Controller 50)

The controller 50 is the center of the control system of the visual function examination apparatus 1. The controller 50 includes, for example, a microprocessor, a RAM, a ROM, a hard disk drive, a communication interface, and the like. The controller 50 includes a main controller 51 and a storage unit 52.

(Main Controller 51)

The main controller 51 performs various kinds of controls. In particular, the main controller 51 controls the light source unit 11, the horizontal scanner 14, the vertical scanner 16, the biological information detector 40, the data processor 60, and the user interface 70. Further, the main controller 51 performs a process of writing data in the storage unit 52 and a process of reading out data from the storage unit 52.

As for controlling of the light source unit 11, the main controller 51 performs control of turning on/off of the output of the laser light, control of changing the output intensity of the laser light, control of changing the output wavelength of the laser light, and the like. The main controller 51 controls the horizontal scanner 14 and the vertical scanner 16 so as to scan the laser light in a preset mode. The scan mode is, for example, a raster scan. As for controlling the biological information detector 40, the main controller 51 performs control of turning on/off of detection of biological information, control of changing the detection intervals of the biological information, control of changing the types of the biological information to be detected, and the like. As for controlling the data processor 60, the main controller 51 performs control of switching the types of processing, control of switching the contents of processing, and the like. As for controlling the user interface 70, the main controller 51 performs control for displaying information on a display unit 71. The main controller 51 controls a corresponding unit of the visual function examination apparatus 1 according to the contents of the operation performed by the use of an operation unit 72.

(Storage Unit 52)

The storage unit 52 stores various kinds of data. Subject information is an example of the data stored in the storage unit 52. The subject information includes, for example, information related to the subject such as identification information of and electronic medical record information of the subject, and information related to the subject's eye such as identification information of the left eye/right eye. Further, the storage unit 52 stores a computer program(s) and data for operating the visual function examination apparatus 1.

The storage unit 52 also stores data (examination data) acquired by examination(s) performed on the subject in the past. The examination data includes, for example, image data obtained by imaging the subject's eye, analysis data obtained by analyzing image data, data obtained by examination(s) other than imaging, and the like.

The image data includes, for example, OCT data acquired by optical coherence tomography, fundus image data obtained by fundus photography, anterior segment image data obtained by anterior segment photography, and the like.

Note that the storage unit 52 may also store arbitrary kinds of image data other than the typical kinds of image data described here as examples.

The analysis data includes, for example, the following types of data. Analysis data obtained from the OCT data of the fundus includes, for example, layer thickness distribution data (that is, data representing the distribution of thickness of a predetermined layer of the fundus), ONH shape data (that is, data representing the shape of the optic nerve head), lesion distribution data (that is, data representing the distribution of lesions), drusen distribution data (that is, data representing the distribution of drusens which are precursor lesions of age-related macular degeneration), lamina cribrosa morphology data (that is, data representing the morphology of the lamina cribrosa), and the like. Analysis data obtained from the OCT data of the anterior segment includes, for example, corneal shape data (that is, data representing the shape of the cornea), corneal endothelial cell data (that is, data representing the number of and/or the shape of corneal endothelial cells), corner angle data (that is, data representing the value of the corner angle, etc.), opacity distribution data (that is, data representing the distribution of opacity sites of the cornea, the crystalline lens, or the like), and the like. It should be noted that the storage unit 52 may store arbitrary kinds of analysis data other than the typical kinds of analysis data described here as examples. For example, the storage unit 52 may store data representing the morphology of and/or the distribution of an arbitrary site such as the meibomian glands, data representing the morphology of and/or the distribution of lesions at an arbitrary site such as the vitreous body, or the like.

The data obtained by examination other than imaging includes, for example, data acquired by static visual field examination, data acquired by dynamic visual field examination, data acquired by flicker perimetry, data acquired by subjective optometry, data acquired by objective optometry, and the like. Note that the storage unit 52 may also store arbitrary types of data acquired by examination other than the typical kinds of examinations described here as examples.

(Data Processor 60)

The data processor 60 performs various kinds of data processing. The data to be processed includes, for example, data acquired by the visual function examination apparatus 1, data input from an external device, data input by a user, and the like. The data processor 60 includes a microprocessor, a RAM, a ROM, a hard disk drive, a circuit board, and the like. A storage device such as the hard disk drive stores a computer program(s) for a microprocessor to execute data processing. The data processor 60 includes an evaluation information generator 61.

(Evaluation Information Generator 61)

Figure 3:
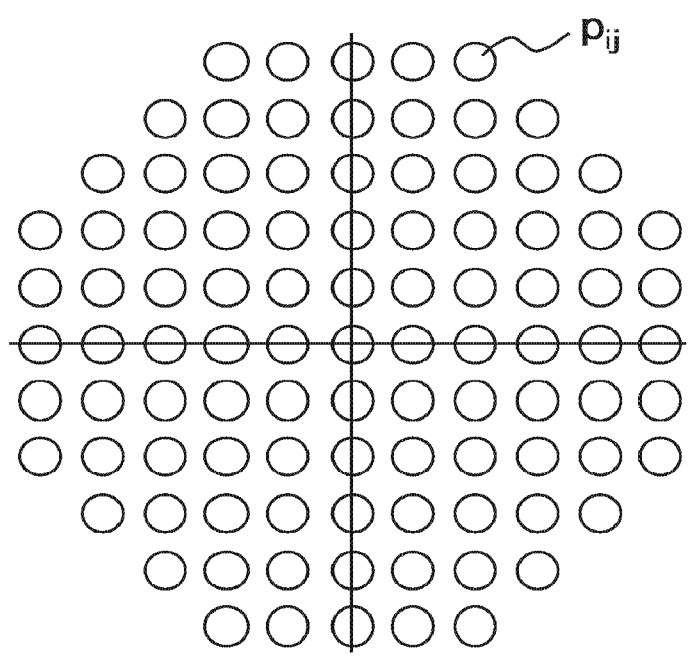
FIG. 3 is a schematic diagram for describing an operation of the visual function examination apparatus according to the embodiment.

The evaluation information generator 61 generates evaluation information on the visual function of the subject's eye E, based on the biological information detected by the biological information detector 40. In the present embodiment, the case of performing the static visual field examination will be described in detail in particular. When the static visual field examination is performed, the distribution of photosensitivity in the retina is obtained as the evaluation information. More specifically, the evaluation information in the case where the static visual field examination is performed is, for example, information representing photosensitivity at each of a plurality of stimulation points $p_{ij}$ (i=1, 2, 3, . . . ; j=1, 2, 3, . . . ) arranged two-dimensionally on the retina in a pre-determined pattern as shown in FIG. 3. The processing executed by the evaluation information generator 61 will be described later.

(User Interface 70)

The user interface 70 is an interface for exchanging information between the visual function examination apparatus 1 and the user. Part of or the whole of the user interface 70 may be provided outside the visual function examination apparatus 1. For example, a configuration can be employed in which a computer (a desktop computer, a laptop computer, a tablet computer, a smartphone, or the like) capable of communicating with the visual function examination apparatus 1 has part of or all of the functions of the user interface 70. The user interface 70 includes the display unit 71 and the operation unit 72.

The display unit 71 includes a display device such as a liquid crystal display or an organic electroluminescence display. The display unit 71 displays information under control of the main controller 51. The display unit 71 may be configured as part of the visual function examination apparatus 1 or may be provided as a peripheral equipment of the visual function examination apparatus 1. In addition, the display unit 71 may include two or more display devices.

The operation unit 72 is used for a user to perform operation input and information input. The operation unit 72 may include buttons and keys provided on the housing of the visual function examination apparatus 1 or outside thereof. The operation unit 72 may be configured as part of the visual function examination apparatus 1 or may be provided as a peripheral equipment of the visual function examination apparatus 1. Further, the operation unit 72 may include two or more operation devices.

The display unit 71 and the operation unit 72 need not be configured as separate devices. For example, a device like a touch panel, which has both a display function and an operation function integrated, may be employed. In that case, the operation unit 72 includes a touch panel and a computer program(s). The main controller 51 controls the touch panel functioning as the display unit 71 to display a graphical user interface (GUI). When the user performs an operation using the GUI, an electric signal corresponding to the operation contents is input to the controller 50. The main controller 51 performs control based on the electric signal.

[Usage Mode]

Figure 4:
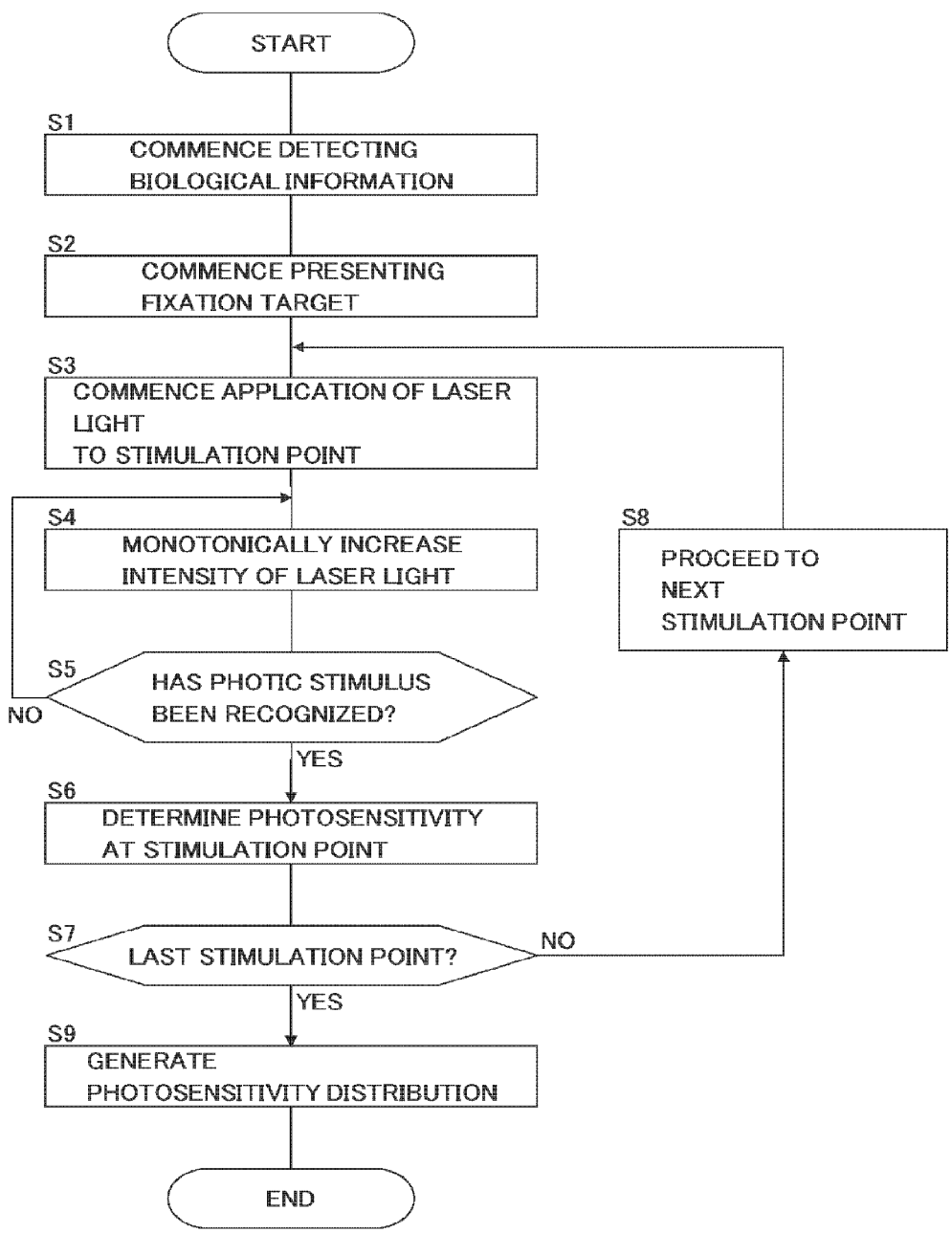
FIG. 4 is a flowchart illustrating an example of a usage mode of the visual function examination apparatus according to the embodiment.

A usage mode of the visual function examination apparatus 1 will be described. The flowchart shown in FIG. 4 shows an example of the usage mode in the case where the static visual field examination is performed using the visual function examination apparatus 1. It is assumed that the position adjustment (alignment) between the subject's eye E and the application optical system 10 has already been made so that the laser light can be properly applied to the retina Er.

(S1: Commence Detecting Biological Information)

First, the main controller 51 controls the biological information detector 40 to commence detecting biological information of the subject. The biological information detector 40 performs iterative detection of the biological information. The iterative detection is performed, for example, at predetermined time intervals. The biological information detector 40 sends the biological information (sampling results) acquired at predetermined time intervals to the main controller 51 in real time. The main controller 51 sends the biological information successively input from the biological information detector 40 to the evaluation information generator 61 in real time. The sampling frequency (iteration rate of detection) of the biological information can be set to an arbitrary value.

As a specific example, the biological information detector 40 functions as an electroencephalograph and acquires a potential difference between a plurality of electrodes arranged on the subject's head at a sampling frequency of several tens of hertz to several hundreds of hertz. The biological information detector 40 sends the sampling results to the main controller 51 in real time. The main controller 51 can control the display unit 71 to display the waveforms representing the electroencephalogram of the subject on the basis of the sampling results successively input from the biological information detector 40. In addition, the main controller 51 can store the sampling results successively input from the biological information detector 40 (or the waveforms based thereon) in the storage unit 52. Further, the main controller 51 sends the sampling results successively input from the biological information detector 40 to the evaluation information generator 61 in real time.

(S2: Commence Presenting Fixation Target)

The main controller 51 commences presenting the fixation target to the subject's eye E. The fixation target corresponds to, for example, a fixation position for positioning the macula center (that is, the fovea centralis) of the subject's eye E on the extended line of the optical axis of the application optical system 10.

In the present embodiment, the fixation target may be a bright spot or an image projected on the retina Er by the application optical system 10. The application optical system 10 can present the fixation target while presenting a predetermined background image to the subject's eye E. This process will be described with reference to FIG. 5.

Figure 5:
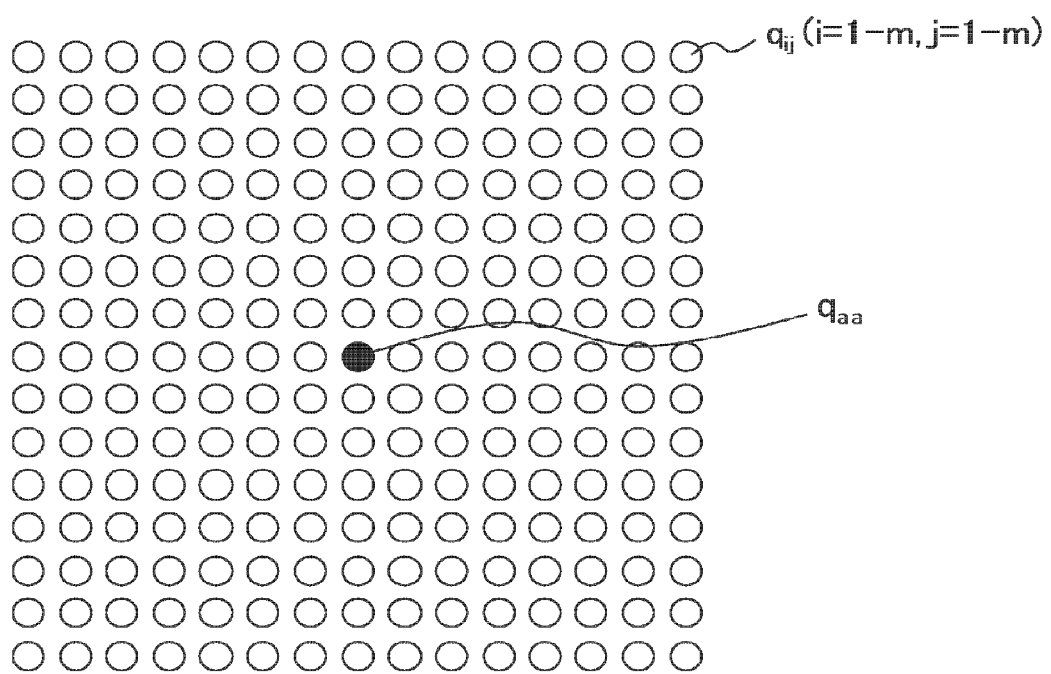
FIG. 5 is a schematic diagram for describing a usage mode of the visual function examination apparatus according to the embodiment.

FIG. 5 shows an arrangement pattern of the target points $q_{ij}$ of the laser light on the retina Er. In this example, a plurality of target points are arranged in m-rows×m-columns. Here, m is an odd number, and a target point $q_{aa}$ (a=(m+1)/2) is arranged at the center of the arrangement pattern. The application optical system 10 sequentially projects the laser light to m×m number of target points $q_{ij}$ by performing raster scan. Further, in this raster scan, while applying the laser light to the target point $q_{aa}$ under the application condition for the fixation target set in advance, the application optical system 10 applies the laser light to other target points $q_{ij}$ (i, j=1 to m; i, j≠a) under the application condition for the background set in advance. The application optical system 10 repeats such raster scan at a predetermined repetition rate. Thereby, while recognizing the background image based on the plurality of target points $q_{ij}$ (i, j=1 to m; i, j≠a), the subject recognizes the fixation target based on the target point $q_{aa}$.

The number of target points for the fixation target may be two or more. Also, the arrangement pattern of the target points is not limited to "odd number×odd number", but may be "odd number×even number", "even number×odd number" or "even number×even number". When any one or both of the number of rows and the number of columns in the arrangement pattern is an even number, the target point(s) for the fixation target may be any of the target points included in the arrangement pattern, or may be a target point(s) provided separately from the arrangement pattern. In the former case, one or more target points adjacent to the center position of the arrangement pattern can be used as the target point(s) for the fixation target. In the latter case, a target point(s) for the fixation target can be provided at or near the center position of the arrangement pattern.

(S3: Commence Application of Laser Light to Stimulation Point)

The main controller 51 commences applying the photic stimulus to the subject's eye E in a state where the fixation target is presented. Here, the arrangement pattern of a plurality of stimulation points is preset. The plurality of stimulation points are the targets to each of which photic stimulus is to be applied, that is, are the examination targets of photosensitivity. The application of photic stimulus is performed in parallel with presentation of the background image and of the fixation target. Such a process is executed by switching the raster scan in step S2 to the raster scan shown in FIG. 6, for example.

Figure 6:
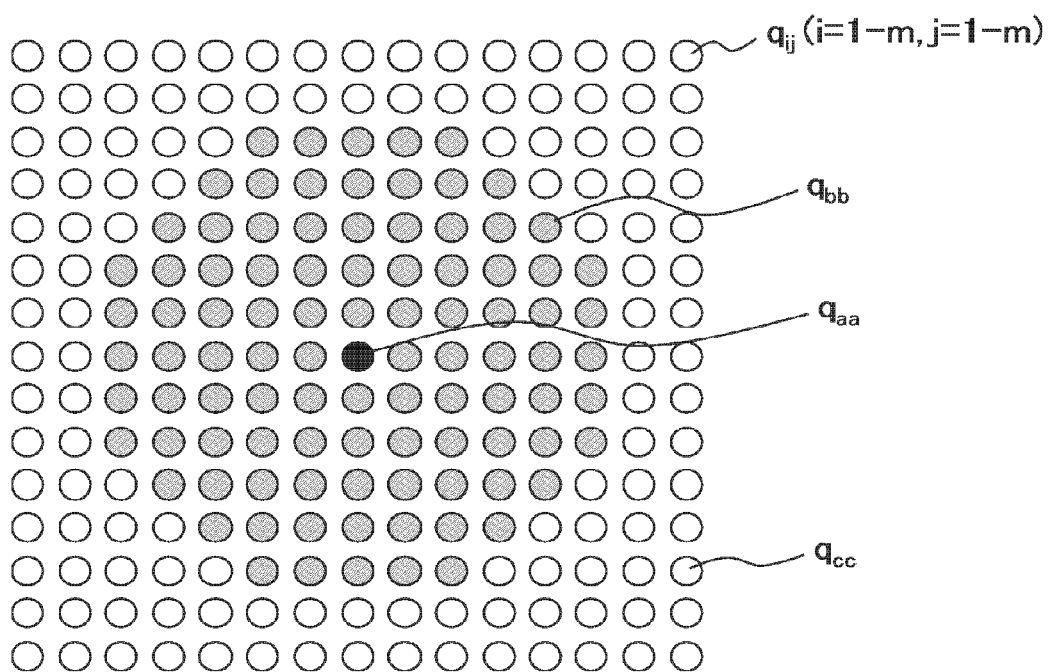
FIG. 6 is a schematic diagram for describing a usage mode of the visual function examination apparatus according to the embodiment.

In FIG. 6, m×m number of target points $q_{ij}$, similar to those in FIG. 5, are classified into the target points $q_{cc}$ for the background, the target point $q_{aa}$ for the fixation target, and the target points (stimulation points) $q_{bb}$ for the photic stimulation. Here, the target point $q_{aa}$ for the fixation target is the same as that in FIG. 5. The target points $q_{bb}$ for the photic stimulation are part of the target points $q_{ij}$ (i, j=1 to m; i, j≠a) for the background in FIG. 5. The target points $q_{cc}$ for the background are a plurality of target points obtained by excluding the target points $q_{bb}$ for the photic stimulation from the target points $q_{ij}$ (i, j=1 to m; i, j≠a) for the background in FIG. 5. When photic stimulus is applied to the position corresponding to the fixation target (the fovea centralis), the laser light for the photic stimulation is projected onto the target point $q_{aa}$ for the fixation target.

Figure 7:
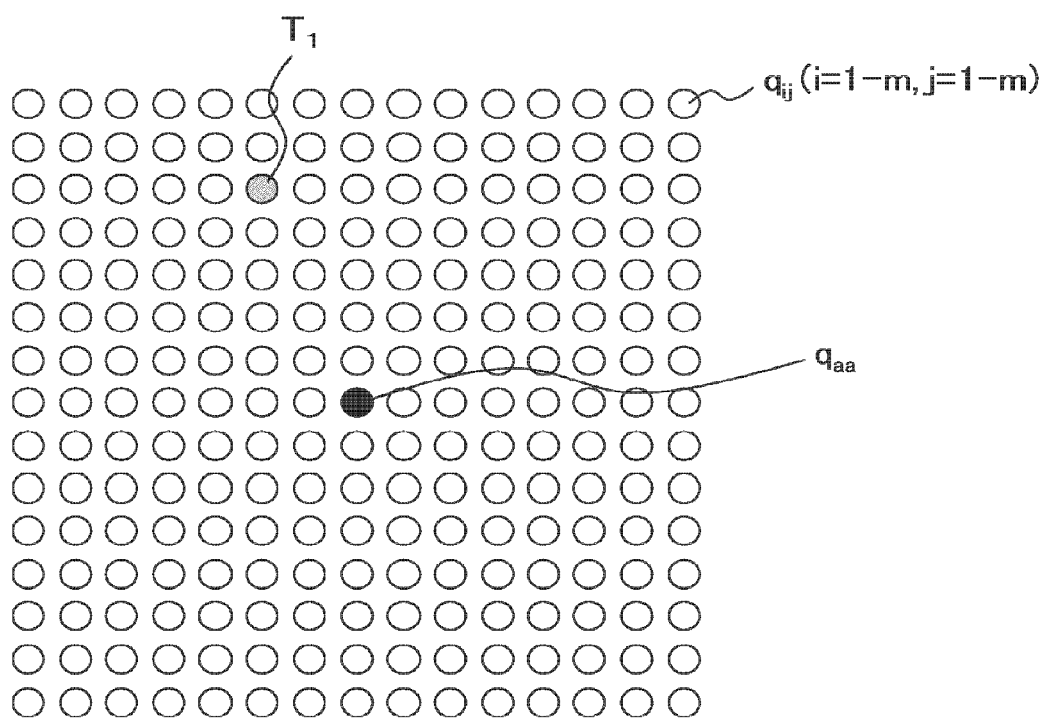
FIG. 7 is a schematic diagram for describing a usage mode of the visual function examination apparatus according to the embodiment.

In the raster scan of this example, when the time is fixed, there is one target point to which photic stimulus is applied. In other words, a plurality of target points $q_{bb}$ for the photic stimulation are ordered in advance, and photic stimulus is applied one by one according to the order. Accordingly, at the timing just after going on from step S2 to step S3, as shown in FIG. 7, the application optical system 10 performs raster scan so as to apply the laser light in the following manner: to apply the laser light to the target point $q_{aa}$ for the fixation target under the application condition for the fixation target set in advance; to apply the laser light to the first target point $T_1$ for the photic stimulation (the first target point $T_1$ is any one of the target points $q_{bb}$ for the photic stimulation) under the application condition for the photic stimulation set in advance; and to apply the laser light to target points $q_{ij}$ (≠$q_{aa}$, ≠$T_1$) other than $q_{aa}$ and $T_1$ under the application condition for the background set in advance. The application optical system 10 repeats such raster scan at a predetermined repetition rate. At this time, the application condition for the fixation target and the application condition for the background both may be constant. On the other hand, the application condition for the photic stimulus can be changed in a way described later.

(S4: Monotonically Increase Intensity of Laser Light)

In step S3, the application optical system 10 commences application of the laser light to the target point $q_{bb}$ for photic stimulation from a predetermined initial intensity. The initial intensity is set to a low intensity such that the subject does not recognize the photic stimulus. In step S4, the main controller 51 controls the application optical system 10 (light source unit 11) so as to monotonically increase the intensity of the laser light applied to the target point $q_{bb}$ for photic stimulation. The monotonic increase may be a continuous increase or a stepwise increase. The rate of increase in the continuous increase may be set to an arbitrary value. The increase interval in the stepwise increase may be set to an arbitrary value.

When the subject recognizes the photic stimulus with the laser light of the initial intensity (the recognition is detected as a change in biological information described later), the main controller 51 can reduce the intensity of the laser light until the subject does not recognize the photic stimulus. Alternatively, when the subject recognizes the photic stimulus by the laser light of the initial intensity, the main controller 51 may perform the process of step S4 so as to monotonically decrease the intensity of the laser light. In this case, step S5 is performed so as to detect the fact that the subject no longer recognizes the photic stimulus.

(S5: Has Photic Stimulus been Recognized?)

The biological information detector 40 has commenced detecting the biological information in step S1 and the detection is continuing at present. In other words, the biological information detector 40 acquires a time course (i.e., change depending on time) of biological information in real time. The biological information acquired in real time is sent successively to the evaluation information generator 61 via the main controller 51.

When the intensity of the laser light is increased in step S4, that is, when the intensity of the photic stimulus with respect to the stimulation point $T_1$ is increased, the biological information changes at the stage when the subject has recognized the photic stimulus. This change corresponds to the transition from the unrecognized state to the recognized state with respect to the photic stimulus. The transition appears as "specific change" in the time course of the biological information acquired by the biological information detector 40.

The pattern of the specific change is preset based on, for example, clinical data. The clinical data may be standard data (e.g., statistical data) obtained from examination of a large number of subjects, or may be individual data obtained for each subject. When the biological information is an electroencephalogram, the pattern of the specific change is expressed as, for example, the shape of the waveform, the amount of change in the potential difference, the rate of change in the potential difference, or the like.

The evaluation information generator 61 accumulates the biological information input to the evaluation information generator 61 in real time via the main controller 51, and monitors the time course of the biological information. Specifically, the evaluation information generator 61 determines whether or not the biological information accumulated along the time series exhibits the above-mentioned "specific change". The determination process is executed, for example, by determining whether or not the biological information accumulated along the time series exhibits a specific pattern.

While the evaluation information generator 61 determines that a specific change is not exhibited, the intensity of the laser light is further increased (S5: NO, and S4). The monotonic increase in the intensity of the photic stimulus continues until the evaluation information generator 61 determines that a specific change has been exhibited in step S5 (S5: YES).

(S6: Determine Photosensitivity at Stimulation Point)

When the subject has been determined to have recognized the photic stimulus (S5: YES), the evaluation information generator 61 generates sensitivity information at the stimulation point $T_1$. The sensitivity information is information representing the photosensitivity at the stimulation point, and may be information in a form similar to the conventional static visual field examination, for example.

When, for example, the photosensitivity at the stimulation point is extremely low, the subject may not recognize the photic stimulus even if the intensity of the laser light is increased up to a predetermined maximum value. Considering such a case, the evaluation information generator 61 may be configured to generate sensitivity information indicating "no photosensitivity" or sensitivity information indicating "photosensitivity is extremely low", when the intensity of the laser light has increased up to a predetermined value or when a predetermined time has elapsed since the intensity of the laser light has been increased up to a predetermined value.

(S7: Last Stimulation Point?)

As described above, the plurality of target points $q_{bb}$ for the photic stimulation are ordered in advance, and photic stimulus is applied one by one according to the order. The main controller 51 or the data processor 60 determines whether or not the stimulation point at which the sensitivity information has been generated in the immediately preceding step S6 is the last stimulation point in the order.

(S8: Proceed to Next Stimulation Point)

When the main controller 51 or the data processor 60 has determined that the stimulation point (e.g., the first stimulation point $T_1$) at which the sensitivity information has been generated in the immediately preceding step S6 is not the last stimulation point (S7: NO), a process for going on to the next stimulation point is executed (S8). This process includes, for example, a process of changing the application condition corresponding to the current stimulation point (e.g., the stimulation point $T_1$) to the application condition for the background, and a process of changing the application condition corresponding to the next stimulation point to the application condition for the photic stimulation.

Upon completion of the processing in step S8, application of the laser light to the next stimulation point commences (S3). Then, the processing from step S4 to step S7 is executed again. This routine is repeatedly executed until it is determined in step S7 that "the stimulation point is the last stimulation point (S7: YES)". Thereby, the measurement result of the photosensitivity at all the stimulation points $q_{bb}$ shown in FIG. 6 is obtained. Here, the measurement result may include the photosensitivity at the target point $q_{aa}$ for the fixation target.

(S9: Generate Photosensitivity Distribution)

In response to the determination of "YES" in step S7, the evaluation information generator 61 generates, based on the plurality of sensitivity information on the plurality of stimulation points $q_{bb}$ of the retina Er, the information representing the distribution of the sensitivity information in the retina Er (that is, the distribution at the stimulation points $q_{bb}$). The distribution information may be text information or image information. Examples of the text information include list information in which position information of the plurality of stimulation points $q_{bb}$ is associated with photosensitivity, character string information representing the range of a visual field obtained from the plurality of sensitivity information and/or the degrees of photosensitivity, and the like. Further, an example of the image information is map information representing the positions of the plurality of stimulation points $q_{bb}$ and the degrees of photosensitivity. The form of the map information thus configured may be the same as that obtained from the conventional static visual field examination). The information generated in step S9 is an example of evaluation information regarding the visual function of the subject's eye E.

The main controller 51 can store the evaluation information generated in step S9 in the storage unit 52, can display the evaluation information on the display unit 71, can send the evaluation information to an external device, can record the evaluation information in a recording medium, or can print the evaluation information on a printing medium. This concludes the description of the usage mode.

Modification of First Embodiment

Several typical modifications of the first embodiment will be described.

Modification 1

In the above embodiment, the background image and the fixation target are presented to the subject's eye E by the use of the application optical system 10, but it is also possible to configure so as to present the background image and/or the fixation target by other means. The present modification corresponds to an example of such a configuration.

Figure 8:
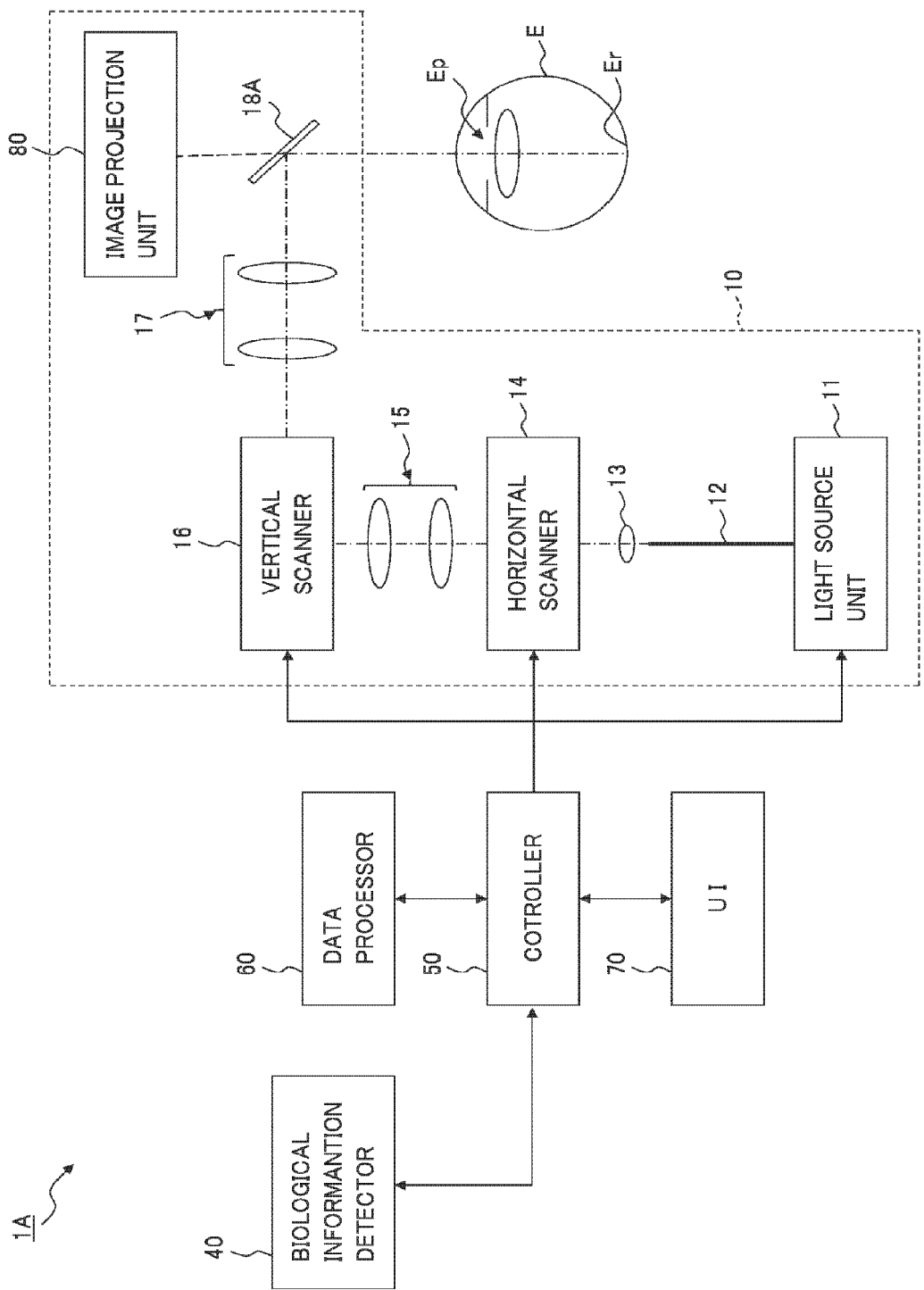
FIG. 8 is a schematic diagram illustrating an example of the configuration of the visual function examination apparatus according to a modification.

FIG. 8 shows an example of the configuration of the visual function examination apparatus according to the present modification. In addition to the configuration shown in FIG. 1, the visual function examination apparatus 1A includes an image projection unit 80. Further, the visual function examination apparatus 1A includes a beam splitter 18A instead of the reflecting mirror 18. The beam splitter 18A combines the optical path formed by the application optical system 10 and the optical path extending from the image projection unit 80. The beam splitter 18A is, for example, a half mirror.

The image projection unit 80 includes, for example, a display device such as a liquid crystal display. Furthermore, the image projection unit 80 includes an optical system for projecting the light emitted from the display device onto the retina Er via the beam splitter 18A. The optical system may include, for example, one or more of a collimating optical system, a relay optical system, a variable magnification optical system, a focus optical system, and an imaging optical system. Further, any of these optical systems may be disposed between the beam splitter 18A and the subject's eye E. Note that the image projection unit 80 may include a retinal scanning display similar to the application optical system 10.

The image projection unit 80 is controlled by the controller 50 (the main controller 51 shown in FIG. 2). The controller 50 controls the image projection unit 80 to project the background image onto the retina Er by displaying a predetermined background image on the display device. Further, the controller 50 controls the image projection unit 80 to project a fixation target onto the retina Er by displaying a bright spot or an image corresponding to the fixation target at a predetermined position (e.g., center position, position on the optical axis, etc.) on the display device.

In the present modification, the application optical system 10 applies photic stimulus to the retina Er and also projects information not presented by the image projection unit 80 onto the retina Er. For example, when the image projection unit 80 projects the background image and the fixation target, the application optical system 10 may be configured so as to perform only the application of the photic stimulus. In addition, when the image projection unit 80 projects only the background image, the application optical system 10 may be configured to apply photic stimulus and to present the fixation target. Further, when the image projection unit 80 projects only the fixation target, the application optical system 10 may be configured to apply the photic stimulus and to present the background image.

At least part of the types of information that can be presented by the application optical system 10 and at least part of the types of information that can be presented by the image projection unit 80 may be common. In that case, information to be presented by the application optical system 10 and information to be presented by the image projection unit 80 may be arbitrarily selected. The selection is performed, for example, by the user or by the controller 50.

In the present modification, the controller 50 (the main controller 51) can control the image projection unit 80 and the application optical system 10 so as to perform the projection of the background image and the application of the photic stimulus in parallel. Furthermore, the controller 50 (the main controller 51) can control the image projection unit 80 and the application optical system 10 so as to perform the projection of the background image, the application of the photic stimulus and the presentation of the fixation target in parallel.

Modification 2

In the usage mode (FIG. 4) of the embodiment above, the intensity of the laser light for photic stimulation monotonically increases from a predetermined initial intensity. In this modification, the process of setting the initial intensity will be described.

Figure 9:
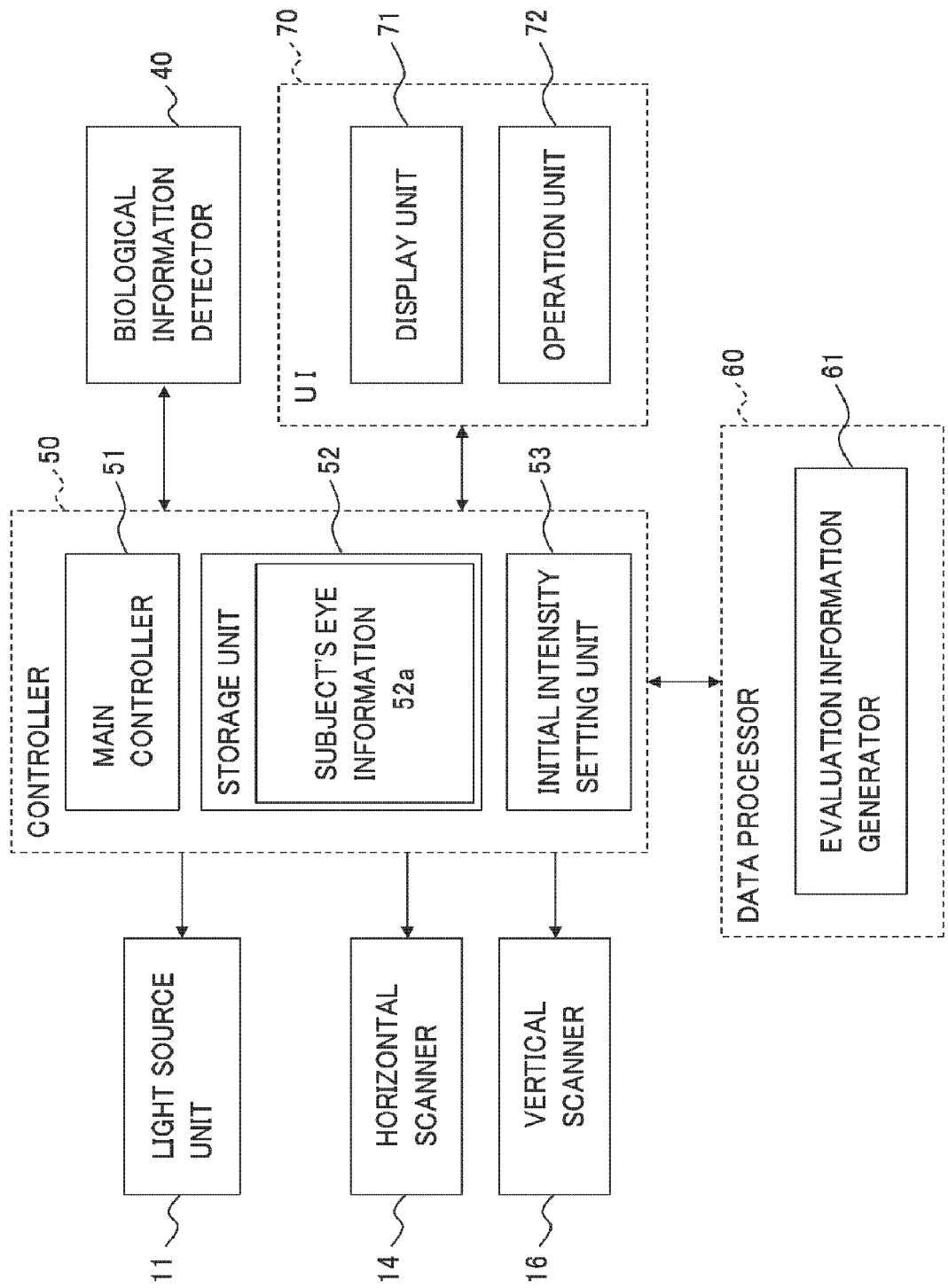
FIG. 9 is a schematic diagram illustrating an example of the configuration of the visual function examination apparatus according to a modification.

FIG. 9 shows an example of the configuration according to the present modification. The configuration shown in FIG. 9, in addition to the configuration shown in FIG. 2, includes an initial intensity setting unit 53. The initial intensity setting unit 53 is provided in the controller 50. In addition, the storage unit 52 stores subject's eye information 52a.

The subject's eye information 52a includes information representing the structure of and/or a function of the subject's eye E. The information representing the structure of the subject's eye E includes, for example, any of the following information: data acquired by OCT of the subject's eye E (OCT data); data acquired by fundus photography of the subject's eye E (fundus image data); data representing the distribution of the thickness of a predetermined layer of the fundus; (layer thickness distribution data); and lesion distribution data representing the distribution of lesions in the fundus. The information representing the function of the subject's eye E includes, for example, any of the following information: data acquired by static visual field examination; data acquired by dynamic visual field examination; and data acquired by flicker visual field measurement.

The initial intensity setting unit 53 sets the initial value of the application intensity of the laser light for photic stimulation based on the subject's eye information 52a. The initial value corresponds to the initial intensity of the laser light employed in step S3 of FIG. 4. Examples of processing executed by the initial sensitivity setting unit 53 will be described below.

The initial sensitivity setting unit 53 refers to information generated in advance. In such reference information, parameters included in the subject's eye information 52a or parameters acquired based on the subject's eye information 52a are associated with the initial intensity. For example, the reference information includes table information in which the aforementioned parameters and initial intensity values are associated with each other, or graph information in which the aforementioned parameters and initial intensity values are associated with each other. The storage unit 52 or the initial intensity setting unit 53 stores the reference information in advance.

As a specific example of the reference information, the case will be described where the parameter included in the subject's eye information 52a or the parameter acquired based on the subject's eye information 52a is the layer thickness distribution data. Research on and accumulation of data for the relationship between the thickness of a predetermined layer of the retina and photosensitivity have been progressing. In general, it is known that photosensitivity decreases with the thinning of a predetermined layer. The reference information is generated based on standard data (e.g., statistical data such as average value, median value, mode, etc.) acquired through research or the like. A value of the initial intensity is set, for example, to a value lower than the value of the photosensitivity corresponding to this initial intensity value. The difference between the value of photosensitivity and the value of initial intensity is set, for example, based on statistical data representing variation (e.g., standard deviation, variance, etc.).

Figure 10B:
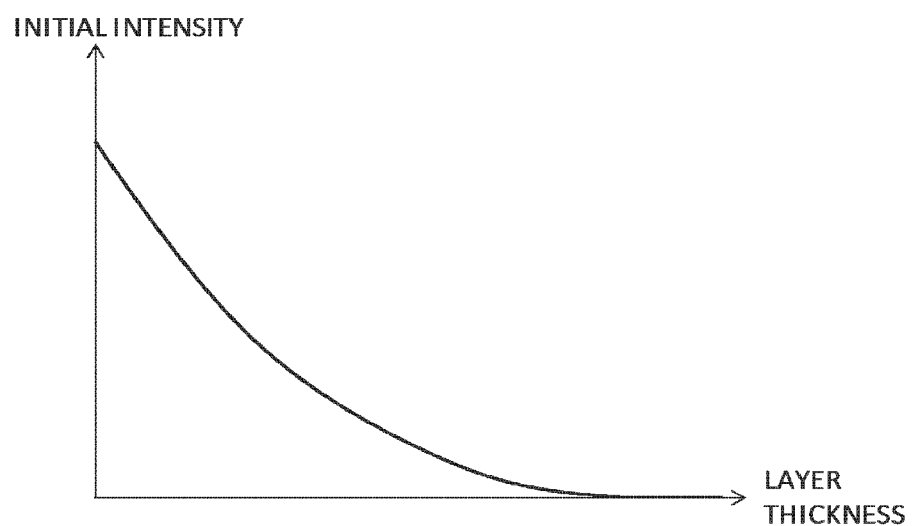
FIG. 10B is a schematic diagram illustrating an example of the configuration of the visual function examination apparatus according to a modification.

Specific examples of reference information are shown in FIG. 10A and in FIG. 10B. The reference information shown in FIG. 10A is table information that associates a parameter indicating the thickness of a predetermined layer of the retina with the initial intensity. The table information includes a column of the parameter "layer thickness d" and a column of the parameter "initial intensity". Values of the layer thickness parameter d (d≥0) are divided into n number of sections. The initial intensity values $B_1, B_2, \ldots, B_n$, which are different from each other, are associated with the n number of sections of the layer thickness parameter d, respectively.

The initial intensity setting unit 53 receives the layer thickness distribution data of the retina Er. The layer thickness distribution data includes the value of layer thickness at the fovea centralis. The initial intensity setting unit 53 associates the position of the fovea centralis in the layer thickness distribution data with the position of the fovea centralis in the arrangement pattern of the plurality of stimulation points (see FIG. 3 and FIG. 6). In addition, the initial intensity setting unit 53 performs scale adjustment between the layer thickness distribution data and the stimulation point arrangement pattern, when necessary. The scale adjustment is carried out, for example, by causing the positions in the layer thickness distribution data corresponding to two or more feature points of the retina Er and the positions in the stimulation point arrangement pattern corresponding to the two or more feature points to coincide with each other. Alternatively, the scale adjustment may be performed based on the scale of the layer thickness distribution data (measurement magnification of OCT, etc.). Thus, the position adjustment between the layer thickness distribution data and the stimulation point arrangement pattern is completed. Next, the initial intensity setting unit 53 acquires the layer thickness value corresponding to each stimulation point in the stimulation point arrangement pattern from the layer thickness distribution data. Subsequently, the initial intensity setting unit 53 specifies the section of the layer thickness parameter d including the acquired layer thickness value for each stimulation point, and obtains the initial intensity corresponding to the section specified. The obtained value of the initial intensity is stored in the storage unit 52 in association with the stimulation point arrangement pattern, for example. When the laser light for photic stimulus is applied to one stimulation point in step S3, the main controller 51 controls the light source unit 11 so as to output the laser light of the initial intensity obtained for the stimulation point. Thereby, the initial intensity obtained for each stimulation point can be applied.

The reference information shown in FIG. 10B is graph information that associates a parameter indicating the thickness of a predetermined layer of the retina (horizontal axis indicating the layer thickness) with the initial intensity (vertical axis). The initial intensity setting unit 53 receives the layer thickness distribution data of the retina Er, performs the position adjustment between the layer thickness distribution data and the stimulation point arrangement pattern, and obtains the value of layer thickness corresponding to each stimulation point in the stimulation point arrangement pattern from the layer thickness distribution data. The process up to this stage is executed in the same way as above. Subsequently, the initial intensity setting unit 53 obtains the initial intensity corresponding to the acquired value of layer thickness from the graph information for each stimulation point. The obtained value of the initial intensity is stored in the storage unit 52 in association with the stimulation point arrangement pattern, for example. The control related to the application of the laser light for photic stimulation is the same as above.

Another example of the process of setting the initial intensity will be described. This example refers to the time course of layer thickness of the retina Er. It is assumed that layer thickness distribution data acquired in the past and photosensitivity distribution acquired substantially at the same time are stored in the storage unit 52. Further, it is assumed that the storage unit 52 stores the latest layer thickness distribution data. In this case, the initial intensity setting unit 53 may be configured to obtain the difference between the past layer thickness distribution data and the latest layer thickness distribution data, to correct the photosensitivity distribution based on the difference, and to set the initial intensity of each stimulation point based on the corrected photosensitivity distribution.

Modification 3

In the above embodiment, the photosensitivity is examined for all of a plurality of stimulation points (see FIG. 3 and FIG. 6) set in advance, but the site to be examined for photosensitivity changes according to the state of the subject's eye. In this modification, a configuration that enables arbitrary setting of stimulation points according to the state of the subject's eye will be described. In this modification, the photic stimulus is applied only to the stimulation points set according to the state of the subject's eye.

Figure 11:
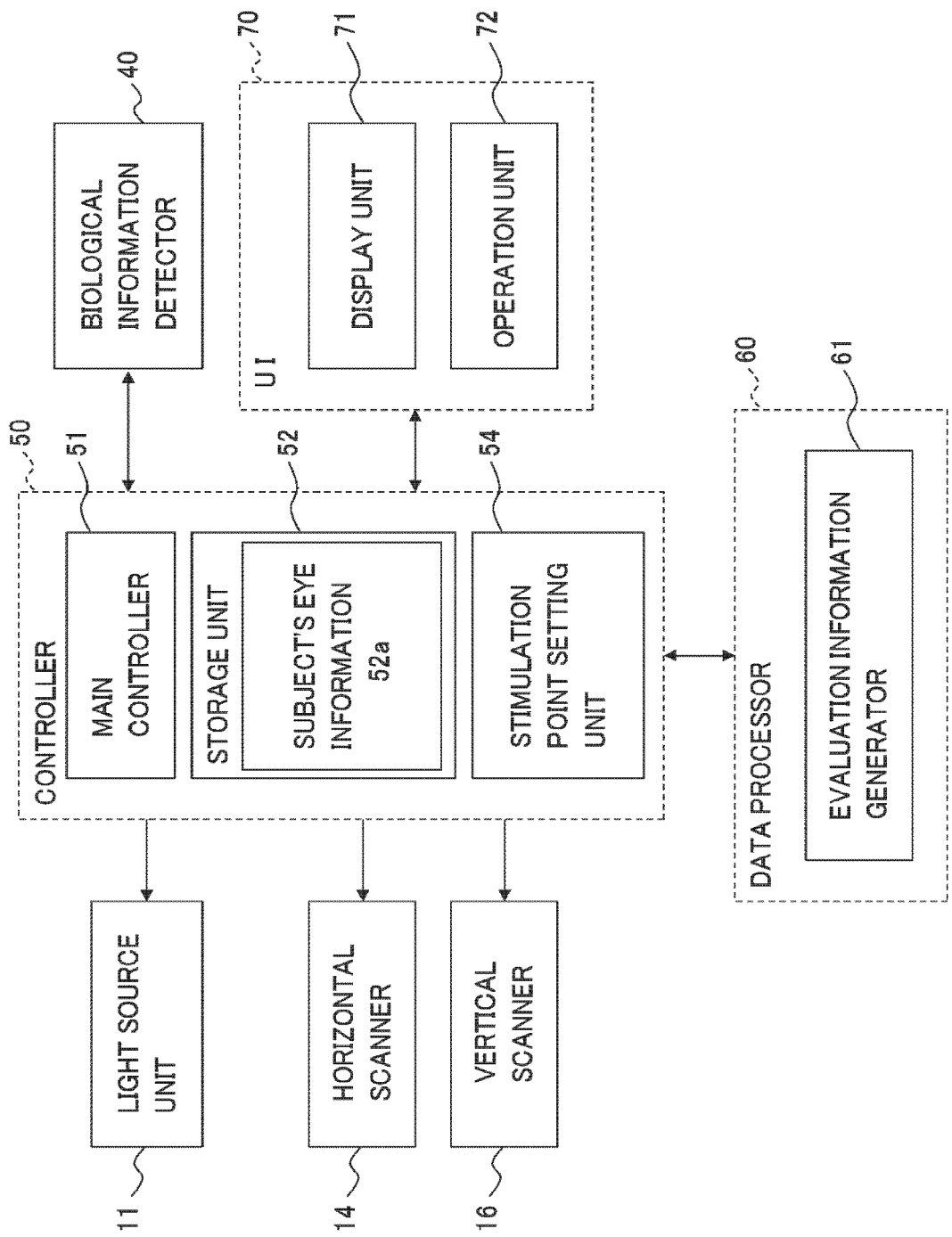
FIG. 11 is a schematic diagram illustrating an example of the configuration of the visual function examination apparatus according to a modification.

FIG. 11 shows an example of the configuration according to the modification. The configuration shown in FIG. 11 includes, in addition to the configuration shown in FIG. 2, a stimulation point setting unit 54. The stimulation point setting unit 54 is included in the controller 50. The storage unit 52 stores subject's eye information 52a which is the same as that of the modification 2.

The stimulation point setting unit 54 sets one or more stimulation points for the laser light to be applied based on the subject's eye information 52a. The setting of the stimulation point(s) is performed by selecting one or more stimulation points from a plurality of stimulation points included in a preset template (see FIG. 3 and FIG. 6), for example. Alternatively, the setting of the stimulation point(s) can be performed without using such a template. Further, the setting of the stimulation point(s) is not limited to setting the position of the stimulation point(s). For example, it may be configured to set the density of the arrangement of the stimulation points according to the site to be examined.

The stimulation point setting unit 54 receives the layer thickness distribution data of the retina Er, for example, performs the position adjustment between the layer thickness distribution data and the stimulation point arrangement pattern (e.g., template), and obtains the value of layer thickness corresponding to each stimulation point in the stimulation point arrangement pattern from the layer thickness distribution data. The process up to this stage is executed in the same way as in the second modification.

Subsequently, the stimulation point setting unit 54 compares the corresponding layer thickness value with a predetermined threshold value for each stimulation point. When the layer thickness value is equal to or less than the threshold value at a particular stimulation point, the stimulation point setting unit 54 sets the stimulation point as an examination target. Through this processing, it is possible to set a portion where the layer is thin as an examination target.

As another example of processing, the stimulation point setting unit 54 compares the value of past layer thickness and new value of layer thickness for each stimulation point. When the difference between them exceed the threshold value at a particular stimulation point, the stimulation point setting unit 54 sets the stimulation point as an examination target. Through this processing, a portion where the layer thickness has changed can be set as an examination target. It should be noted that the configuration may be so that the stimulation point is set as the examination target only in the case where the layer thickness has decreased.

Further, it is possible to employ a configuration in which, without using a template, a stimulation point is set at a portion where the value of layer thickness is equal to or less than the threshold value or at a portion where the value of layer thickness has changed. Further, it is possible to configure so as to set two or more sections concerning layer thickness values, to set stimulation points with a lower density in a section where the value of layer thickness is larger, and to set a stimulation point with a higher density in a section where the value of layer thickness is smaller.

[Effects]

The effects of the embodiment (and modifications thereof) will be described.

The visual function examination apparatus 1 according to the embodiment includes the application optical system 10, the biological information detector 40, and the evaluation information generator 61. The application optical system 10 includes the optical scanner (the horizontal scanner 14 and the vertical scanner 16) disposed in the optical path of the laser light output from the light source unit 11 (laser light source), and is configured to apply the laser light that has travelled via the optical scanner to the retina Er of the subject's eye E. The biological information detector 40 is configured to detect biological information representing the reaction of the subject to the application of the laser light. The evaluation information generator 61 is configured to generate evaluation information on the visual function of the subject's eye E based on the biological information detected.

According to the visual function examination apparatus thus configured, a photic stimulus can be applied to the retina Er using the technology of the retinal scanning display, the reaction to the photic stimulus can be automatically detected, and based on the detection result, evaluation of the visual function can be performed.

The visual function examination apparatus is configured to apply the photic stimulus by employing the technology of the retinal scanning display. Therefore, applying an appropriate photic stimulus is possible without being affected by the state of the ocular optical system (for example, refraction abnormality such as myopia, hyperopia, astigmatism, etc.). Thereby, the reliability of the examination can be improved. Further, since there is no need to provide a refractive optical system for correcting refraction abnormality, reduction of the error in the evaluation result due to the error in the correction value can be achieved. Furthermore, simplification of the configuration of the apparatus is also possible. In addition, since no time is needed for refraction correction, shortening of the examination time (that is, improvement of the examination efficiency) can also be achieved.

In addition, since the visual function examination apparatus is configured to acquire a reaction to a photic stimulus by automatically detecting biological information, the subject need not press a response button. Therefore, even when the subject is unfamiliar with the examination, is an elderly person, or is tired, the reaction to the photic stimulus can be accurately acquired. Thereby, the reliability of the examination can be improved.

In the embodiment, the biological information detector 40 may be configured to iteratively detect biological information. In this case, the evaluation information generator 61 can be configured to generate the evaluation information based on the time course of the biological information obtained by the iterative detection.

With such a configuration, biological information can be detected at a timing when a reaction to the photic stimulus occurs. As a result, reaction error can be reduced and the reliability of the examination as well as the examination efficiency can be improved.

In the embodiment, the visual function examination apparatus may include the controller 50 for controlling the application optical system 10. The controller 50 is configured to control the application optical system 10 so as to monotonically change the application intensity of the laser light to one stimulation point of the retina Er while the iterative detection of the biological information is performed. Furthermore, the evaluation information generator 61 is configured to generate sensitivity information at the one stimulation point based on the time course of the biological information according to the monotonic change of the application intensity of the laser light, and to generate distribution of the sensitivity information at a plurality of stimulation points based on the sensitivity information generated for each of a plurality of stimulation points of the retina Er. The distribution of sensitivity information is used as evaluation information.

With such a configuration, it is possible to improve the efficiency of the examination and to improve the reliability of the examination. More specifically, with the conventional apparatus, a threshold value of the light intensity which can be visually recognized by the subject is determined by arbitrarily increasing and decreasing the intensity of the photic stimulus to gradually narrowing the permissible range of the threshold value. On the other hand, in the present configuration, the threshold value is specified by monotonically increasing or by monotonically decreasing the intensity of the photic stimulus. Therefore, the process of gradually narrowing the permissible range is not necessary. Thus, it is possible to shorten the examination time, and to avoid errors that may occur during the process of gradually narrowing the permissible range.

In the embodiment, the controller 50 is configured to control the application optical system 10 to apply the laser light to the one stimulation point under the first application condition (application condition for photic stimulation), and to apply laser light to another site of the retina Er under the second application condition (application condition for background) different from the first application condition. In addition, the controller 50 can control the application optical system 10 to iteratively perform these applications.

With such a configuration, the application of photic stimulus and the presentation of the background image both can be performed by the use of the application optical system 10. Note that the background image is, for example, a white background, a black background, a gray background, a color background, a background including a still image, a background including a moving image, or the like. The background image to be presented may be selected, for example, based on the type (or kind) of the examination to be performed. Further, the user may select a desired background image. As an example, by applying a photic stimulus while presenting a moving image portraying daily environment (for example, a moving image simulating the situation of driving a car) as a background image, the state of the visual function under specific environment can be evaluated.

In the embodiment, the controller 50 can control the application optical system 10 so as to go on to the examination of the next stimulation point in response to the generation of the sensitivity information at the one stimulation point. More specifically, the controller 50 may be configured to control the application optical system so as to, in response to the generation of the sensitivity information at the one stimulation point, apply a photic stimulus to a new stimulation point, to apply the laser light to a different site from the new stimulation point to present the background image, and to iteratively perform these applications.

Here, the timing indicated by "in response to the generation of the sensitivity information" is not only the timing at which the sensitivity information has just been generated (generation timing), but may be any of the followings, for example: the timing at which data for generating the sensitivity information (that is, the biological data) is acquired (acquisition timing); any timing between the acquisition timing and the generation timing; and any timing after the generation timing.

In the embodiment, the visual function examination apparatus may include the image projection unit 80 (background image projection unit) configured to project the background image onto the retina Er. In this case, the controller 50 can be configured to control the image projection unit 80 and the application optical system 10 so as to perform the projection of the background image and the application of the laser light in parallel.

According to such a configuration, although the visual function examination apparatus needs to include the image projection unit 80 separately from the application optical system 10, the configuration and control of the application optical system 10 can be simplified. Another advantage of this configuration is that composite information presentation can be performed using the application optical system 10 and the image projection unit 80.

In the embodiment, the visual function examination apparatus may include the storage unit 52 (eye information storage unit) configured to store information representing a structure of or a function of the subject's eye E (the subject's eye information 52a) in advance. In this case, the controller 50 may include the initial intensity setting unit 53 configured to set an initial value of the application intensity of the laser light based on the information stored in the storage unit 52. Furthermore, the controller 50 may be configured to control the application optical system 10 so that the application of the laser light to one stimulation point commences from the initial value and that the application intensity of the laser light then monotonically increases or monotonically decreases.

According to such a configuration, the initial value of the intensity of the photic stimulus can be set in accordance with the structure of or the function of the subject's eye E, so that it is possible to improve the efficiency of the examination.

In the embodiment, when the storage unit 52 stores the subject's eye information 52a, the controller 50 may include the stimulation point setting unit 54 configured to set one or more stimulation points to which the laser light is to be applied based on the subject's eye information 52a. Further, the controller 50 may be configured to control the application optical system 10 so as to apply the laser light to each of the one or more stimulation points set.

According to such a configuration, it is possible to perform the examination for only the stimulation points considered to be necessary in the light of the state of the subject's eye E. Note that it is possible to configure such that the user can arbitrarily change (add, delete, etc.) one or more stimulation points that have been automatically set. In that case, for example, the controller 50 may control the display unit 71 to display a reference image such as an OCT image, a fundus image, layer thickness distribution, or the like. Furthermore, the controller 50 may control the display unit 71 to display, on the reference image, a stimulation point image(s) indicating the position(s) of the one or more stimulation points that have been automatically set. The user can add or delete a simulation point using the operation unit 72.

Features and effects of the present embodiment are not limited to those described above. For example, any of the configurations and effects described in the present embodiment and the modifications thereof, and furthermore, any of aspects/matters that can be directly or indirectly conceived by persons skilled in the art based thereon, are included in the configuration and effects of the present embodiment.

Second Embodiment

In the present embodiment, a visual function examination apparatus capable of executing a dynamic visual field examination will be described. The visual function examination apparatus according to the present embodiment may include the same optical system as that of the first embodiment (see, for example, FIG. 1 and FIG. 8).

Figure 12:
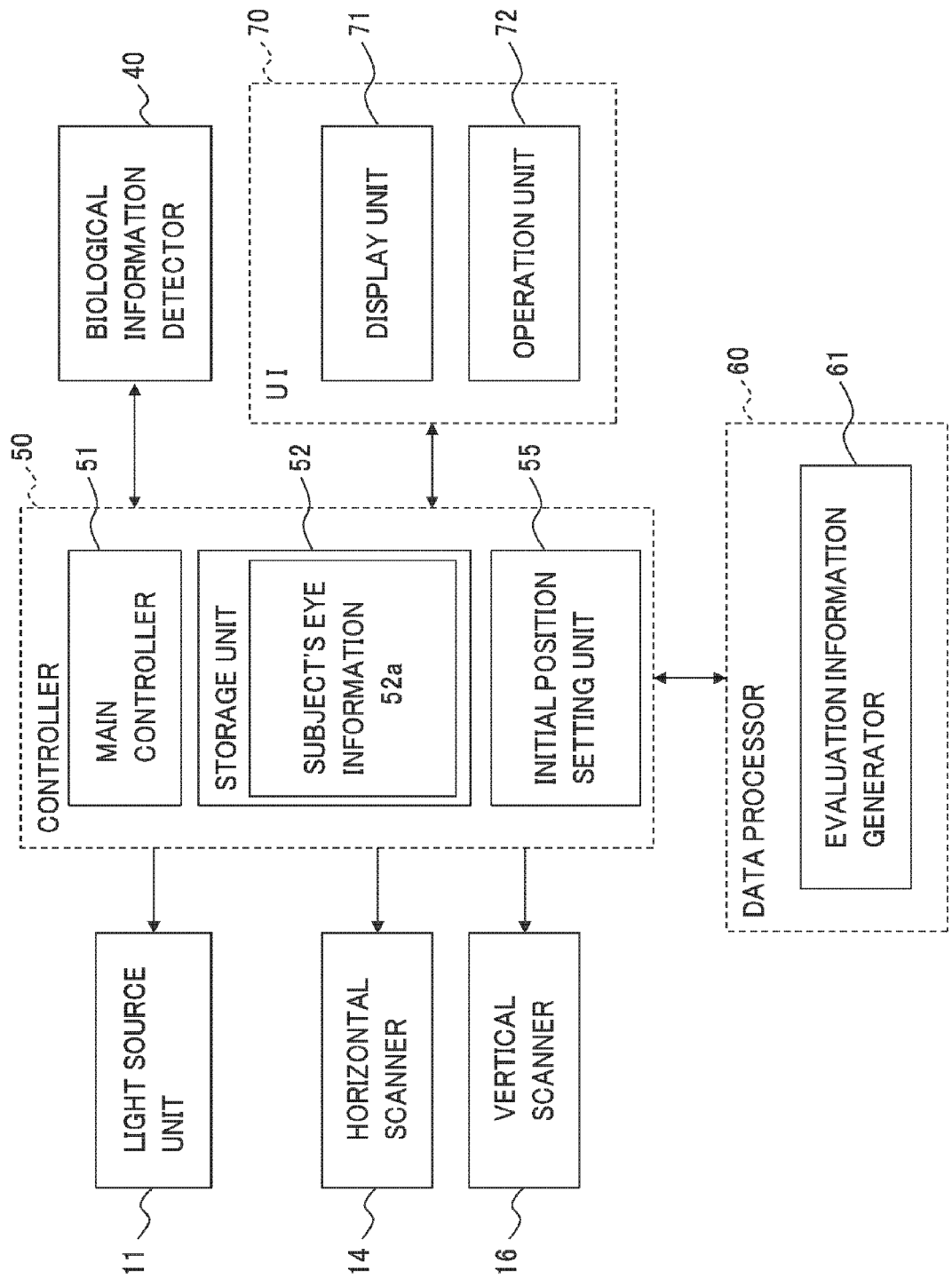
FIG. 12 is a schematic diagram illustrating an example of the configuration of the visual function examination apparatus according to an embodiment.

An example of the configuration of the control system according to the present embodiment is shown in FIG. 12. The configuration shown in FIG. 12 includes, in addition to the configuration shown in FIG. 2, an initial position setting unit 55. The initial position setting unit 55 is included in controller 50. The storage unit 52 stores the subject's eye information 52a same as that in the first embodiment.

The biological information detector 40 iteratively performs detection of biological information. The controller 50 (the main controller 51) is configured to control the application optical system 10 so as to continuously change the application position of the laser light with respect to the retina Er while the iterative detection of the biological information is performed. For example, similar to the conventional dynamic visual field examination, the controller 50 controls the application optical system 10 so as to commence the application of the laser light from a position deviated from the visual field of the subject's eye E and to move the application position toward the center of the visual field or the vicinity of the center. As a specific example, the outermost position (edge) in the scannable range is set as the initial position of the application of the laser light, and moves the application position toward the center position of the visual field.

The evaluation information generator 61 obtains information representing the range of the visual field of the subject's eye E based on the time course of the biological information according to the continuous change of the application position of the laser light. The type of information used for this process is different from the conventional dynamic visual field examination. More specifically, in the conventional dynamic visual field examination, an operation signal input by the subject's pressing the button has been used for processing. On the other hand, in the present embodiment, the biological information automatically detected is used for processing. As with the conventional dynamic visual field examination, the evaluation information generator 61 can generate information (image) representing the outer edge of the visual field as evaluation information.

The initial position setting unit 55 sets the initial position of the application of the laser light based on the subject's eye information 52a. As a specific example, the initial position setting unit 55, for example, receives layer thickness distribution data of the retina Er, and specifies positions that are located away from the center of the visual field (the fovea centralis) by a predetermined distance in the layer thickness distribution data and that the value of the layer thickness is equal to or less than a threshold value. Further, the initial position setting unit 55 specifies one position on a predetermined movement path of the photic stimulus from among the specified positions. This specified position (the one position specified) is set as the initial position in the movement path. The initial position setting unit 55 executes such processing for each of a plurality of movement paths.

For each of the movement paths, the controller 50 is configured to control the application optical system 10 so as to commence the application of the laser light on the retina Er from the corresponding initial position.

According to the visual function examination apparatus of the present embodiment, it is possible to set the initial position for moving the laser light according to the structure of or the function of the subject's eye E in the dynamic visual field examination. Therefore, it is possible to improve the efficiency of dynamic visual field examination.

Third Embodiment

In the first and second embodiments, the visual function examination apparatus configured to apply the photic stimulus to the left eye or the right eye has been described. On the other hand, in the present embodiment, a configuration capable of applying photic stimuli to both eyes of a subject in parallel will be described. The meaning of "applying photic stimuli to both eyes in parallel" includes both "performing the application of the photic stimuli to the both eyes at the same time", and "performing the application of the photic stimulus to the left eye and that to the right eye in a switching manner (in an alternate manner)".

Figure 13:
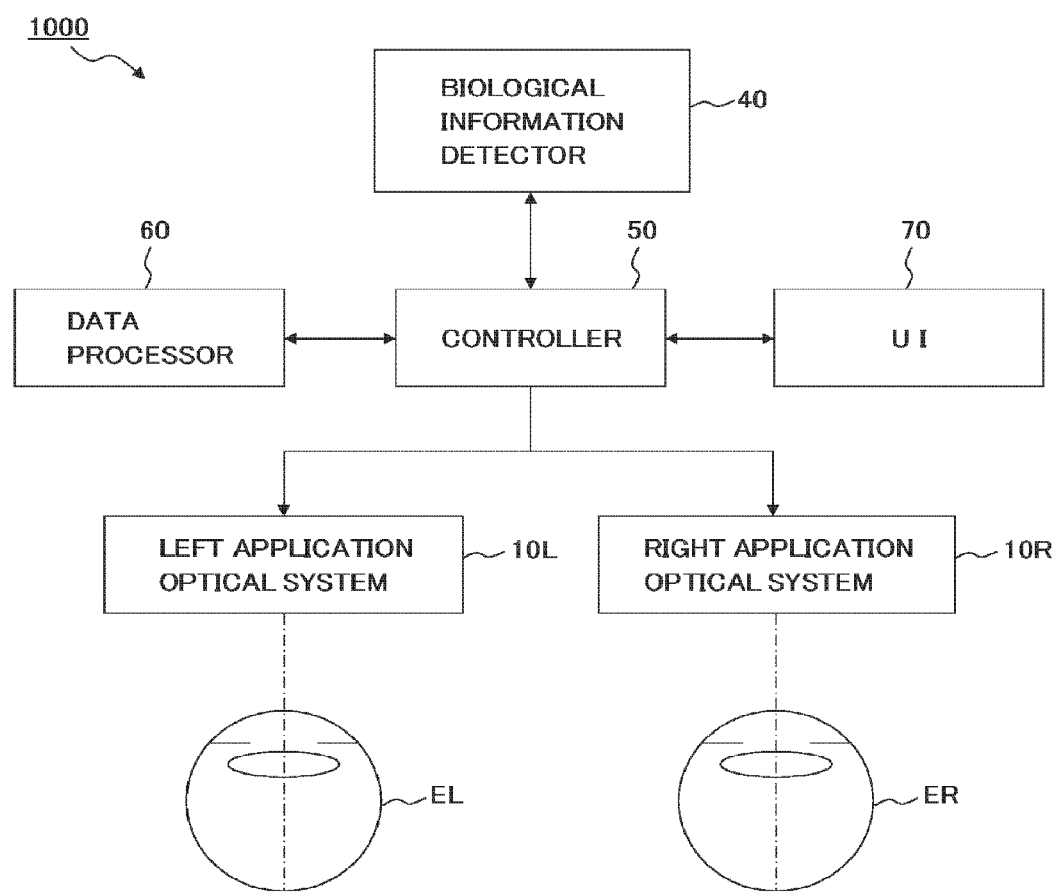
FIG. 13 is a schematic diagram illustrating an example of the configuration of the visual function examination apparatus according to an embodiment.

FIG. 13 shows an example of the configuration according to the present embodiment. The visual function examination apparatus 1000 shown in FIG. 13 includes a pair of left and right application optical systems, namely, a left application optical system 10L and a right application optical system 10R. The left application optical system 10L is used for applying the laser light to the retina of the left eye of the subject (left eye EL), and the right application optical system 10R is used for applying the laser light to the retina of the right eye of the subject (right eye ER). Each of the left application optical system 10L and the right application optical system 10R may have the same configuration as the application optical system 10 of the first embodiment (see FIG. 1). The controller 50 can independently control the left application optical system 10L and the right application optical system 10R. The controller 50 can also control the left application optical system 10L and the right application optical system 10R in an interlocking way. The biological information detector 40, the controller 50, the data processor 60, and the user interface 70 may also be configured in the same manner as with the first embodiment.

The configuration shown in FIG. 13 includes the left and right application optical systems separately, but the configuration according to the present embodiment is not limited thereto. In other words, it is possible to adopt a configuration in which at least part of the optical system for applying the laser light to the left eye EL and at least part of the optical system for applying the laser light to the right eye ER are common. An example of such a configuration is shown in FIG. 14.

Figure 14:
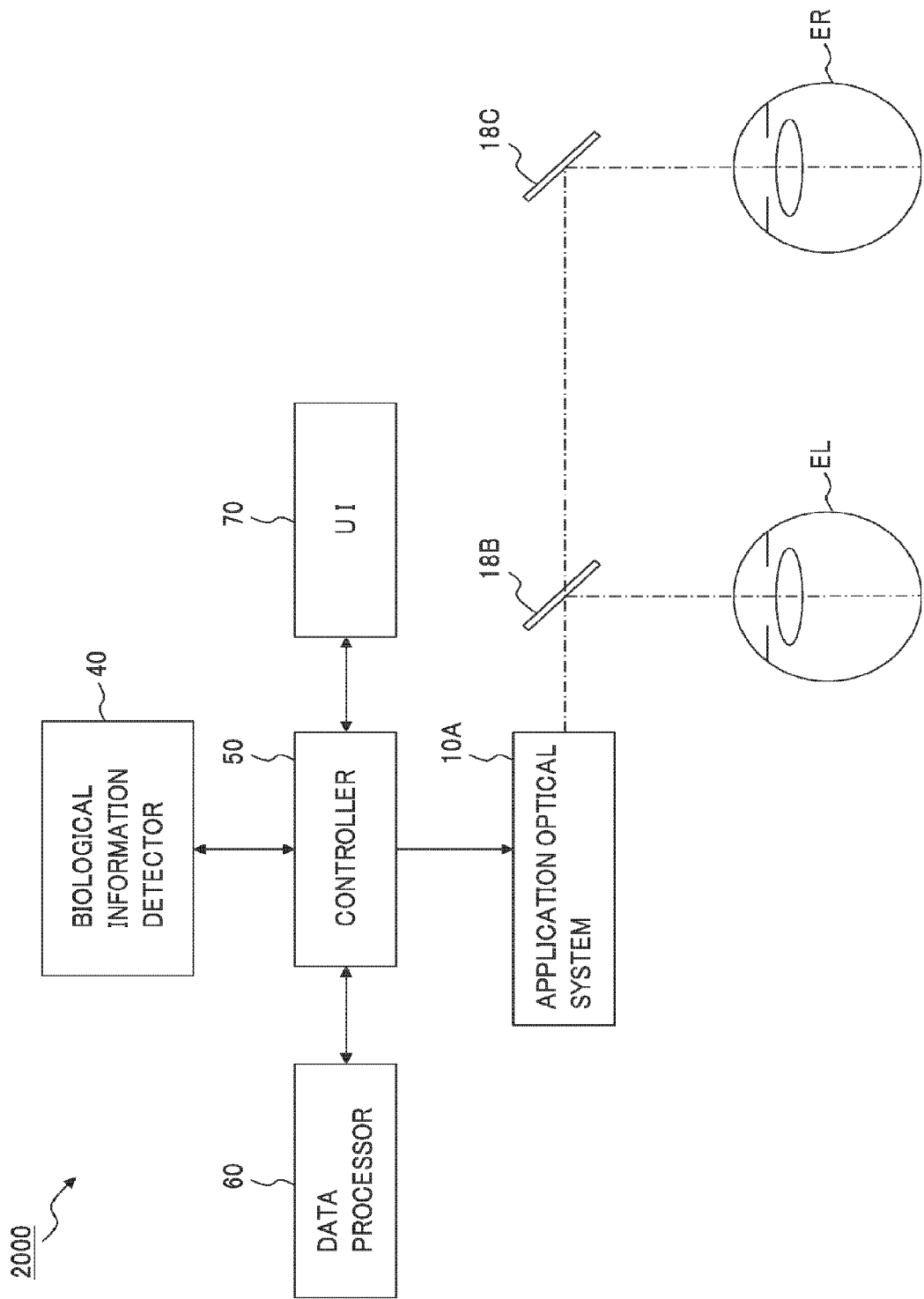
FIG. 14 is a schematic diagram illustrating an example of the configuration of the visual function examination apparatus according to the embodiment.

The application optical system 10A of the visual function examination apparatus 2000 shown in FIG. 14 includes, for example, components other than the reflecting mirror 18 among the components included in the application optical system 10 of the first embodiment. More specifically, the application optical system 10A may include the light source unit 11, the optical fiber 12, the collimating optical system 13, the horizontal scanner 14, the relay optical system 15, the vertical scanner 16, and the relay optical system 17.

Further, the visual function examination apparatus 2000 includes a beam splitter 18B and a reflecting mirror 18C. The beam splitter 18B is arranged in front of the left eye EL, and the reflecting mirror 18C is arranged in front of the right eye ER. The beam splitter 18B is, for example, a half mirror. It should be noted that by employing a dichroic mirror as the beam splitter 18B, laser light having different wavelengths can be applied to the left eye EL and the right eye ER. Further, by employing a polarization beam splitter as the beam splitter 18B, laser light having different polarization states can be applied to the left eye EL and the right eye ER. It is also possible to employ a deflecting mirror as the beam splitter 18B and/or as the reflecting mirror 18C. With such a configuration, different scanning modes can be applied to the left eye EL and the right eye ER. Note that when a deflecting mirror is employed, it is possible to adopt a configuration excluding part of or all of the functions of the optical scanner in the application optical system 10A.

It is possible to configure so that the interval between the beam splitter 18B and the reflecting mirror 18C is changeable. The interval is arbitrarily changed in accordance with the pupillary distance of the subject. The examiner or the subject can change the interval by hand. Alternatively, the interval can also be changed electrically. In this case, an actuator such as a stepping motor is provided, and the controller 50 performs operation control of the actuator. It is possible to automate the adjustment of the interval in the case where the configuration in which the electrical change of the interval is employed. The automatic interval adjustment is performed, for example, based on the value of pupillary distance measured in advance. Alternatively, it is also possible to monitor the left eye EL and the right eye ER and to perform the automatic interval adjustment. As a specific example thereof, it is possible to provide a device (camera(s)) for imaging the anterior segment of the left eye EL and the anterior segment of the right eye ER. In addition, it is possible to change the interval between the beam splitter 18B and the reflecting mirror 18C based on the left anterior segment image and the right anterior segment image acquired by the camera(s).

Any kinds of optical elements can be arranged between the application optical system 10A and the beam splitter 18B and/or between the beam splitter 18B and the reflecting mirror 18C. Examples of such optical elements include a relay optical system, an imaging optical system, a scanning optical system, and the like.

The laser light output from the application optical system 10A is guided to the beam splitter 18B. Part of the laser light is reflected by the beam splitter 18B, is guided to the left eye EL, and is projected onto the retina of the left eye EL. Other part of the laser light is transmitted through the beam splitter 18B, is guided to the reflecting mirror 18C, is reflected by the reflecting mirror 18C, is guided to the right eye ER, and is projected onto the retina of the right eye ER.

Figure 15:
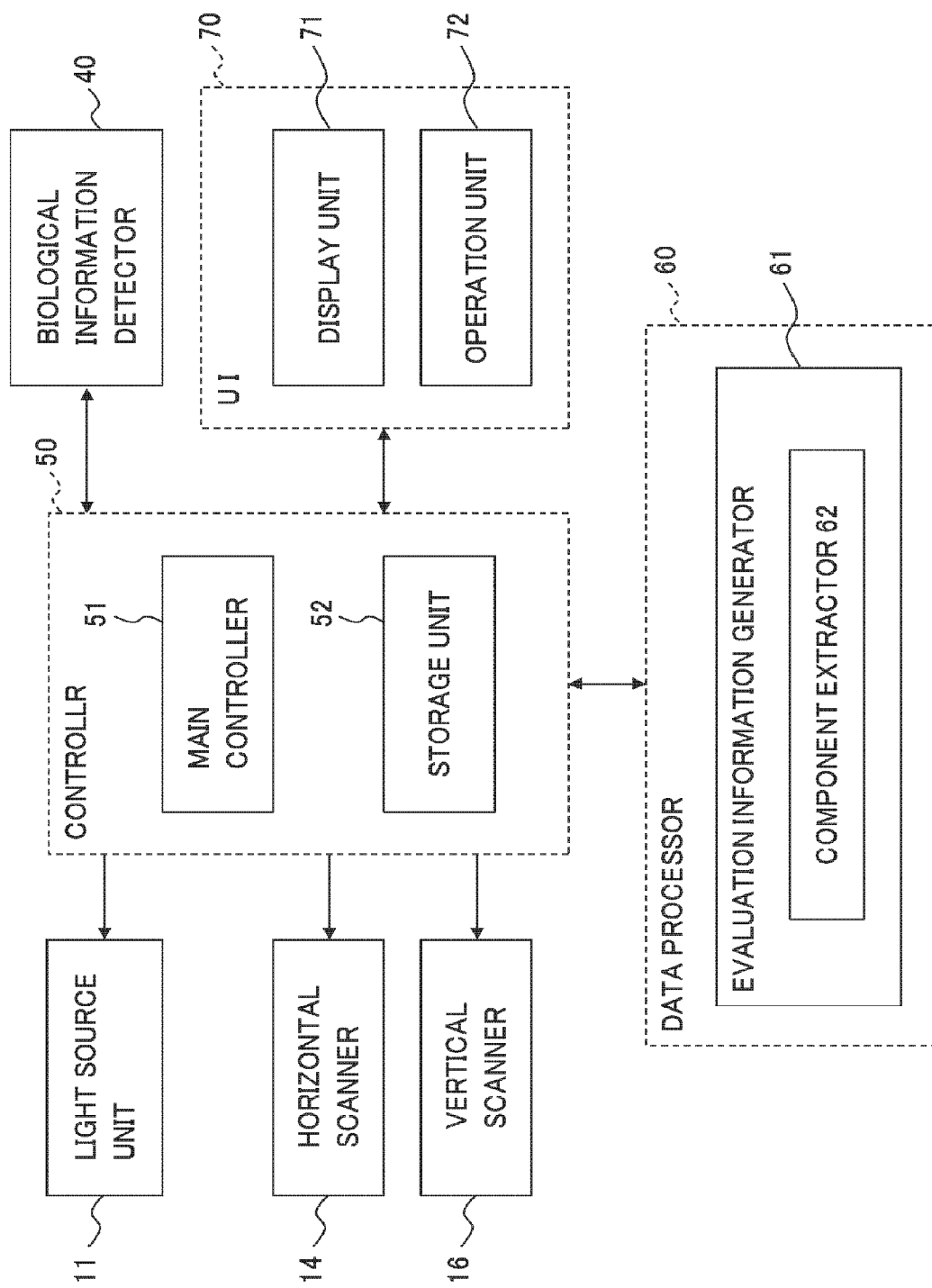
FIG. 15 is a schematic diagram illustrating an example of the configuration of the visual function examination apparatus according to the embodiment.

FIG. 15 shows an example of the configuration of the control system according to the embodiment. The configuration shown in FIG. 15 includes, in addition to the configuration shown in FIG. 2, a component extractor 62. The component extractor 62 is included in the data processor 60.

In the present embodiment, photic stimuli can be applied to the left eye EL and the right eye ER in parallel. When the photic stimuli are simultaneously applied to the left eye EL and the right eye ER, the detected biological information includes the components corresponding to the reaction to a photic stimulus with respect to the left eye EL (left eye components) and the components corresponding to the reaction to a photic stimulus with respect to the right eye ER (right eye components). The component extractor 62 is configured to analyze the biological information to extract the left eye components and the right eye components from the biological information. Extraction of the left eye components is performed based on electroencephalogram components acquired by two or more electrodes corresponding to the sense of sight of the left eye, among a plurality of electrodes attached to the subject's head, for example. Likewise, the extraction of the right eye components is performed based on the electroencephalogram components acquired by two or more electrodes corresponding to the sense of sight of the right eye, for example.

In addition, when the photic stimuli are applied to the left eye EL and the right eye ER in a switching manner, the detected biological information includes the left eye components and the right eye components in a time-divisional way. Switching of the subject's eye to which a photic stimulus is applied is performed by the controller 50. The controller 50 sends the switching signal to the component extractor 62 in real time. Further, biological information iteratively detected is input to the component extractor 62 in real time. The component extractor 62 determines whether the biological information corresponds to either the left eye components or the right eye components based on the input timing of the switching signal and on the input timing of the biological information. Alternatively, the component extractor 62 may be configured to extract the left eye components and the right eye components based on the combination of the electrodes in the electroencephalograph, as in the case where the photic stimuli are applied to the left eye EL and to the right eye ER at the same time.

The evaluation information generator 61 generates evaluation information on the left eye EL (left eye evaluation information) based on the left eye components extracted by the component extractor 62. Furthermore, the evaluation information generator 61 generates evaluation information on the right eye ER (right eye evaluation information) based on the right eye components extracted by the component extractor 62. The process of generating the evaluation information from each of the components is executed, for example, in the same manner as in the first embodiment.

With such a configuration, it is possible to perform the examination of the left eye EL and the examination of the right eye ER individually and in parallel. These examinations may be of the same type or may be of different types. The controller 50 performs control related to each of the examinations. By performing the examination of the left eye EL and the examination of the right eye ER in parallel, it is possible to improve the efficiency of the examination.

Further, according to the present embodiment, it is also possible to perform an examination related to the linkage between the left eye EL and the right eye ER. Such an examination is referred to as binocular visual function examination. The binocular visual function examination includes evaluation of binocular visual fields. In the conventional visual field examination, the left eye and the right eye have been individually evaluated. However, taking into account the fact that the subject uses binocular vision in his/her daily life, it is considered desirable to perform evaluation in a state where both eyes are simultaneously used. In this embodiment, such a binocular visual function examination (binocular visual fields examination) can be realized.

In the binocular visual function examination, in addition to adjusting the interval between the left laser light and the right laser light, it is possible to configure so that the incidence direction of the laser light is changeable. For example, in the configuration shown in FIG. 13, it is possible to induce the vergence of the left subject's eye EL and the right subject's eye ER by having a configuration in which the projecting direction of the laser light output from the left application optical system 10L is changeable and the projecting direction of the laser light output from the right application optical system 10R is changeable and by presenting fixation targets to the left subject's eye EL and to the right subject's eye ER. This makes it possible to perform the binocular visual function examination in such a natural binocular visual state. In the configuration shown in FIG. 14, a similar binocular visual function examination can be realized by employing a deflecting mirror as the beam splitter 18B and a deflecting mirror as the reflecting mirror 18C.

MODIFICATIONS

Several configurations that can be optionally employed to the first to third embodiments will be described below. It should be noted that although modifications will be described based on some of the above embodiments, it goes without saying that the modifications can be employed to other embodiments in similar ways.

Modification 1

The visual function such as the visual field may be affected by the posture of the subject. In the present modification, a configuration for evaluating the visual function taking into account the influence of the posture will be described.

Figure 16:
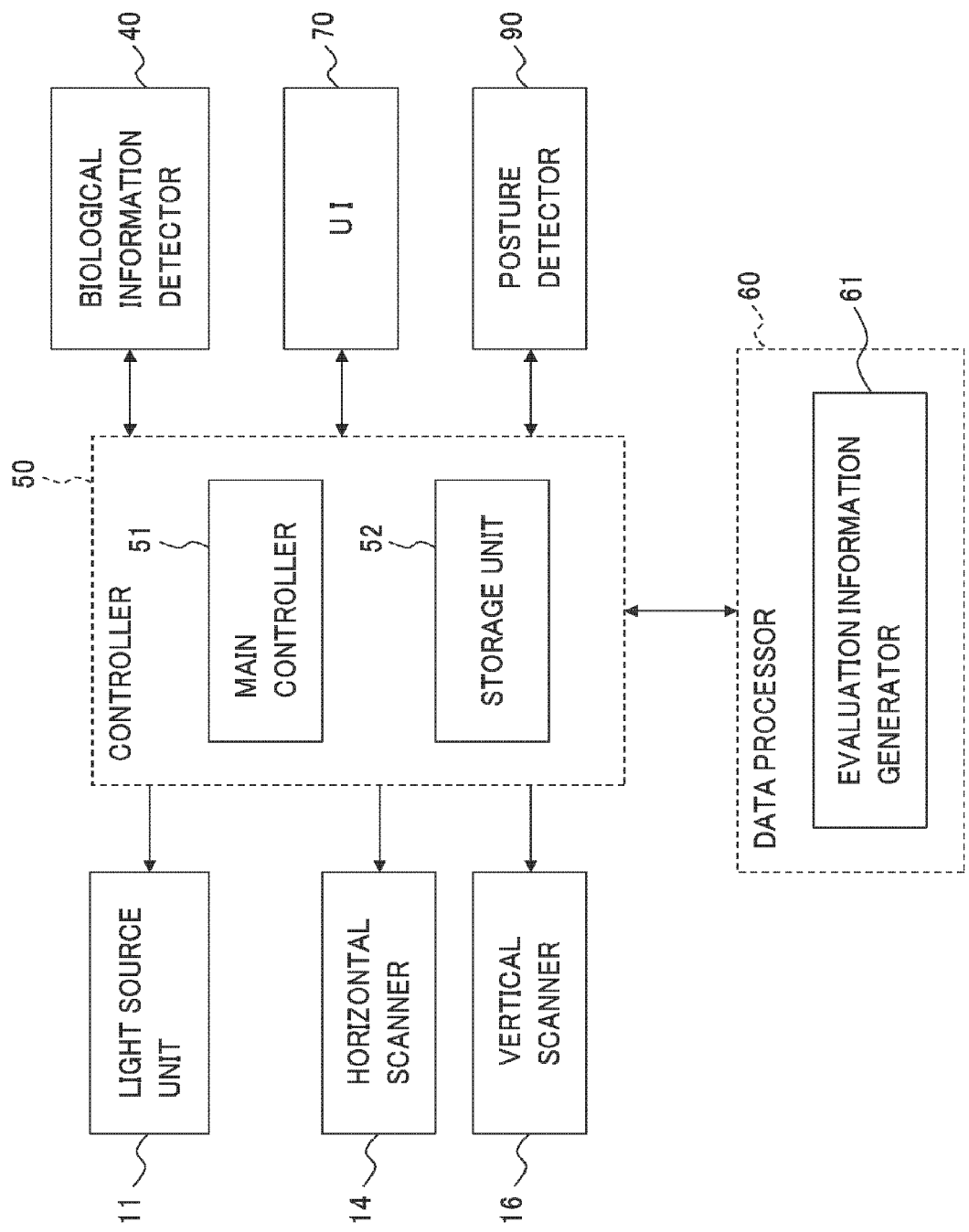
FIG. 16 is a schematic diagram illustrating an example of the configuration of the visual function examination apparatus according to a modification.

FIG. 16 shows an example of the configuration of the control system according to the present modification. The configuration shown in FIG. 16 includes, in addition to the configuration shown in FIG. 2, a posture detector 90. The posture detector 90 has a function of detecting the posture of the subject. As one example, the posture detector 90 includes an acceleration sensor, a gyro sensor, or the like, and is attached to the subject. Alternatively, the posture detector 90 may include a camera for photographing the subject and a processor for determining the posture of the subject by analyzing the photographed image taken by the camera. As another example, the posture detector 90 includes a camera attached to the subject and a processor for determining the posture of the subject by analyzing the photographed image taken by the camera.

The posture detector 90 continuously monitors the posture of the subject or detects the posture of the subject in response to a command from the main controller 51. The detection result of the posture of the subject (posture information) obtained by the posture detector 90 is input to the main controller 51. The main controller 51 associates the evaluation information generated by the evaluation information generator 61 with the posture information acquired when the biological information used for generating the evaluation information is acquired. The main controller 51 controls the storage unit 52 to store the evaluation information and the posture information associated with the evaluation information.

This makes it possible to perceive in what posture the visual function examination has been performed. In addition, it is possible to consider the change in evaluation result according to the difference in posture by carrying out the visual function examination a plurality of times while changing the posture. By referring to evaluation information and posture information acquired in the past, the visual function examination can be performed in the same posture as in the past examination. In particular, the time course of the evaluation results in a specific posture can be perceived in a follow-up observation or in a pre-and-post-operative observation.

Modification 2

The visual function is a complex sensory function realized by the optical system, the nervous system and the brain. In the conventional technology, even when an abnormality is found in the visual function, it has been difficult to specify which site of the visual system has caused the abnormality. In this modification, a configuration that can be employed for specifying an abnormal site of the visual system will be described.

Figure 17:
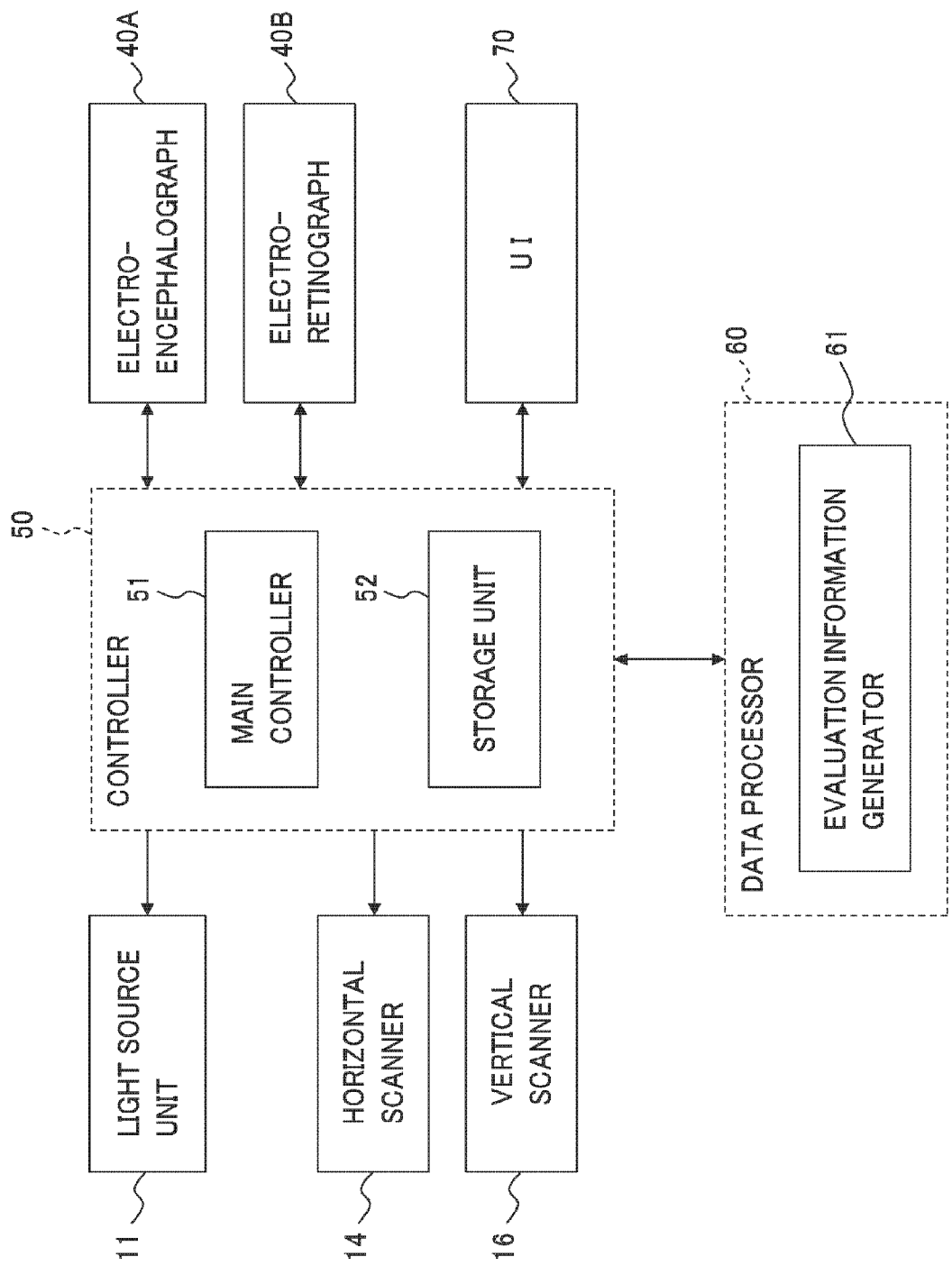
FIG. 17 is a schematic diagram illustrating an example of the configuration of the visual function examination apparatus according to a modification.

FIG. 17 shows an example of the configuration of the control system according to the present modification. The configuration shown in FIG. 17 includes an electroencephalograph 40A and an electroretinograph 40B as the biological information detector 40 in FIG. 2. The electroencephalograph 40A acquires an electroencephalogram representing the electrical activity of the subject's brain. The electroretinograph 40B acquires an electroretinogram representing the electrical activity of the subject's retina. Note that the configuration of the biological information detector 40 is not limited to this, and the biological information detector 40 may be any combination of two or more biological information detectors.

In a usage mode according to the present modification, the visual function examination apparatus performs the measurement with the electroencephalograph 40A and the measurement with the electroretinograph 40B in parallel while performing a visual function examination. In other words, changes in the electroencephalogram and changes in the electroretinogram with respect to photic stimuli applied to the subject's eye are monitored. The following processing for specifying the abnormal site of the visual system is executed by the controller 50 and/or the data processor 60, for example.

In the case where there is an abnormality in the visual function and specific changes in response to the photic stimuli occur in both the electroretinogram and the electroencephalogram, it is deemed that no particular abnormality has occurred in the retina and in the brain. In this case, it is suspected that an abnormality exists in the ocular optical system and/or in the nervous system between the retina and the brain. The abnormality in the ocular optical system can be found with other examination (for example, examination using a slit lamp microscope, fundus camera or OCT). In the case of absence of abnormality in the ocular optical system, it can be considered that the abnormality in the visual function is caused by the nervous system. In the case where a device for detecting the abnormality in the nervous system is equipped in the visual function examination apparatus or in the case where the presence or absence of the abnormality of the nervous system can be obtained externally, it is possible to perform processing in consideration of the presence or absence of the abnormality in the nervous system. Also, when it is considered that there is no abnormality at all sites, it is suspected that the visual function abnormality is psychogenic. It should be noted that the presence or absence of abnormality in the visual function in the present modification may be acquired by another examination (for example, visual field examination with a perimeter).

In the case where there is an abnormality in the visual function and a specific change in response to the photic stimuli occurs only in the electroretinogram, it is deemed that no particular abnormality has occurred in the retina. In this case, it is suspected that an abnormality exists in the brain, in the nervous system and/or in the ocular optical system. Screening for these sites can be performed in the same way as above. It is the same also in the case where a specific change in response to the photic stimuli occurs only in the electroencephalogram.

In the case where there is an abnormality in the visual function and a specific change in response to the photic stimuli does not occur in neither the electroretinogram nor the electroencephalogram, it is suspected that at least abnormality exists in both the retina and the brain. Screening is performed, for example, in the same manner as described above.

As described above, according to the present modification, it is possible to detect two or more different types of biological information and to generate evaluation information concerning each of two or more sites of the visual system based on the detection results of these biological information. Here, the two or more sites of the visual system may be at least two of the ocular optical system, the retina, the nervous system and the brain, for example. Alternatively, it is also possible to perform evaluation by dividing any site into two or more portions.

Modification 3

In the visual function examination, it is important that the fixation of the subject's eye is properly achieved. Further, when the time required for the examination is relatively long like the visual field examination, it is desirable to be able to monitor whether the fixation state is stable. In the present modification, a configuration for satisfying such a demand will be described.

As described in the first embodiment, examples of the device for projecting the fixation target onto the retina (fixation target projection unit) includes the application optical system 10 and the image projection unit 80.

Figure 18:
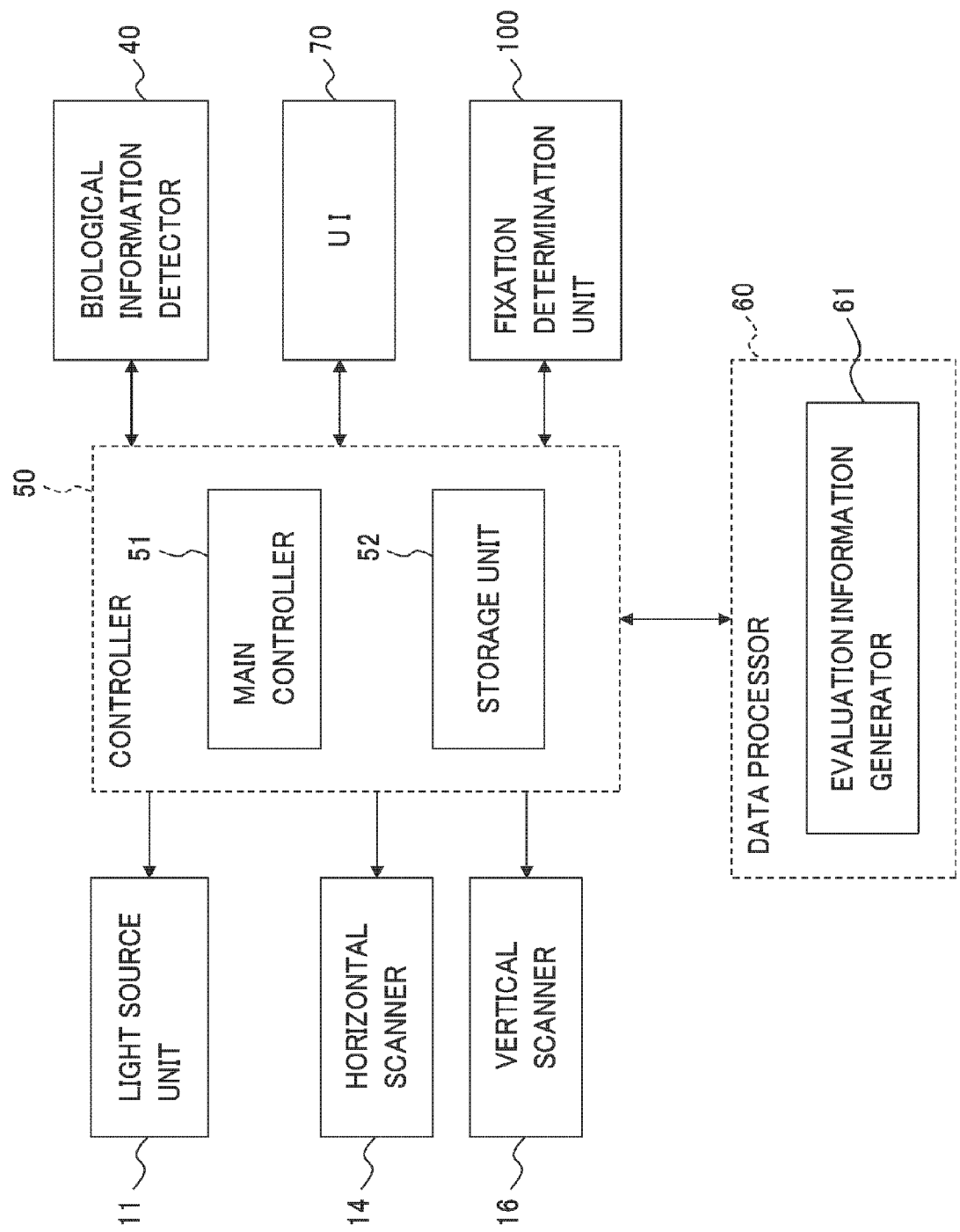
FIG. 18 is a schematic diagram illustrating an example of the configuration of the visual function examination apparatus according to a modification.

FIG. 18 shows an example of the configuration of the control system according to the present modification. The configuration shown in FIG. 18 includes, in addition to the configuration shown in FIG. 2, a fixation determination unit 100. The fixation determination unit 100 determines the fixation state of the subject's eye E in a state where the fixation target is projected. In other words, the fixation determination unit 100 monitors the state of the eye movement of the subject's eye E. Note that the fixation determination unit 100 may further has a function of detecting the state of the eyelids (that is, detecting the occurrence of blinking, the fact that the eyelids are closed, etc.).

The fixation determination unit 100 includes, for example, a camera that captures a moving image of the anterior segment of the subject's eye E and a processor that analyzes the observation image of the anterior segment acquired by the camera in real time. The processor analyzes a frame of the observation image to detect the pupil region (or the pupil center position) in the frame. The processor sequentially executes such processing for successively acquired frames to obtain a time course in the position of the pupil region. When the displacement of the pupil region is included in a predetermined allowable range, the processor determines that fixation of the subject's eye E is stable. On the other hand, when the displacement is not included in the predetermined allowable range, the processor determines that a fixation error has occurred. The processor, for example, inputs a signal (fixation error occurrence signal) to the controller 50 in response to the determination that a fixation error has occurred. Alternatively, the processor repeatedly inputs a signal representing the current fixation state to the main controller 51.

As another example of the fixation determination unit 100, an electrooculogram (eyeball potential diagram) can be employed. The electrooculogram is data representing a chronological variation of the electric potential according to the displacement of the eyeball and is obtained by using a plurality of electrodes arranged around the eye. The fixation determination unit 100 of this configuration includes an electrooculograph for acquiring an electrooculogram and a processor that analyzes the acquired electrooculogram in real time. The processor acquires the displacement of the subject's eye E on the basis of the time course of the electrooculogram acquired in real time and determines whether or not the displacement is included in a predetermined allowable range, thereby detecting the fixation error. The processor, for example, inputs a signal to the controller 50 in response to the determination that a fixation error has occurred. Alternatively, the processor repeatedly inputs a signal representing the current fixation state to the main controller 51.

The main controller 51 sends the signal representing the current fixation state or the signal indicating that a fixation error has occurred to the evaluation information generator 61. In addition, biological information is input to the evaluation information generator 61 in real time. For example, the evaluation information generator 61 discards the biological information input while a fixation error occurred. In other words, the evaluation information generator 61 generates evaluation information based on the biological information acquired when it is determined that the fixation state of the subject's eye E is appropriate.

According to the present modification, the visual function can be evaluated based on the biological information acquired when the fixation state is appropriate. Therefore, the reliability of the examination can be improved.

Modification 4

As described above, it is important to perform the visual function examination in a state where the subject's eye is appropriately fixed. However, interrupting the examination or discarding the biological information every time a fixation error occurs will cause a prolonged examination. In the present modification, a configuration for the target position of the application of the laser light to follow the movement of the subject's eye will be described. With such a configuration, it is possible to continue the examination even when the subject's eye is moving.

Figure 19:
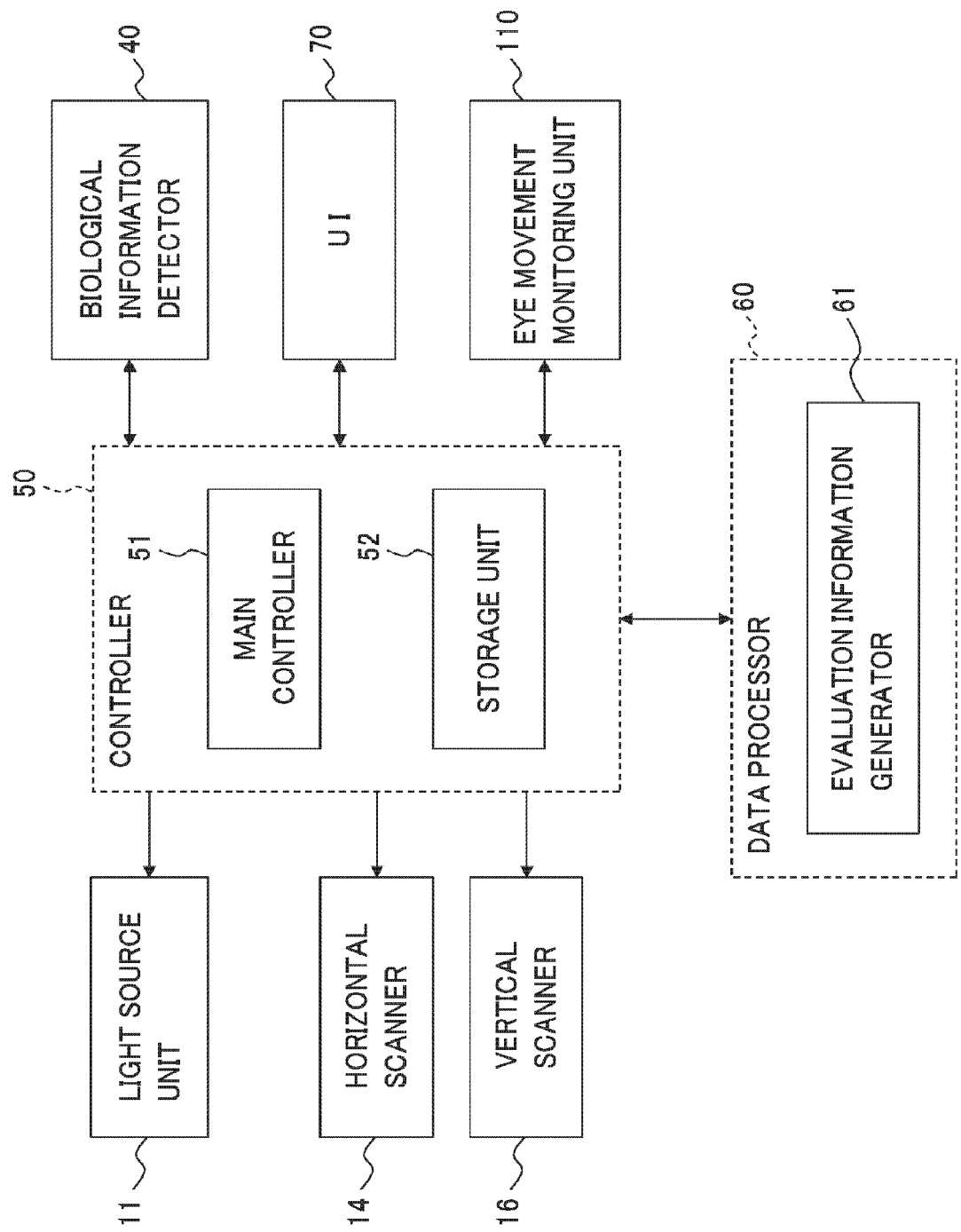
FIG. 19 is a schematic diagram illustrating an example of the configuration of the visual function examination apparatus according to a modification.

An example of the configuration of the control system according to the present modification is shown in FIG. 19. The configuration shown in FIG. 19 includes, in addition to the configuration shown in FIG. 2, an eye movement monitoring unit 110. The eye movement monitoring unit 110 monitors eye movements of the subject's eye E. The eye movement monitoring unit 110 includes, for example, a camera that captures a moving image of the anterior segment of the subject's eye E and a processor that analyzes the observation image of the anterior segment acquired by the camera in real time. The processor analyzes a frame of the observation image to detect the pupil region (or the pupil center position) in the frame. The processor sequentially executes such processing for successively acquired frames to acquire a time course in the position of the pupil region. The processor sends information representing the movement of the subject's eye E (eye movement information) acquired in such a way to the controller 50 in real time. The method of acquiring the eye movement information is not limited to this. For example, an electrooculograph can be employed to acquire the eye movement information.

The main controller 51 controls the horizontal scanner 14 and the vertical controller 16 based on the output from the eye movement monitoring unit 110 (that is, based on the eye movement information). The main controller 51 functions as a scan controller. A specific example of the processing executed by the main controller 51 will be described. The eye movement monitoring unit 110 sends eye movement information representing the current position (the current orientation) of the subject's eye E to the controller 50 at predetermined time intervals and in real time. Upon receipt of new eye movement information, the main controller 51 calculates the displacement between the position represented by the eye movement information input immediately before and the position indicated by the new eye movement information. Then, the main controller 51 performs control of the horizontal scanner 14 and the vertical scanner 16 so as to eliminate the calculated displacement. With this, the position to which the photic stimulus is applied can be shifted in accordance with the eye movement in real time.

In the above example, the position of the photic stimulus is controlled by controlling the optical scanner, but the configuration is not limited thereto. For example, the visual function examination apparatus includes a drive mechanism for moving the application optical system 10. Further, the main controller 51 controls the driving mechanism so as to eliminate the displacement calculated based on the eye movement information. With this, the application optical system 10 can move in accordance with the movement of the subject's eye E.

Modification 5

Part of or the whole of the visual function examination apparatus may be wearable. Certain types of visual function examinations are performed in a darkroom so that the subject is not affected by external light. The visual function examination apparatus according to the present modification is provided for such use.

The visual function examination apparatus according to the present modification includes a shielding unit, holding units, and an attachment unit in addition to the configuration of any of the embodiments described above. The shielding unit, the holding units and the attachment unit are integrally configured.

The shielding unit is configured to have a function of shielding the field of view of the subject's eye E. That is, unlike the inventions disclosed in Japanese Unexamined Patent Publication No. 2012-155019 and US Patent Publication No. 2013/0044042 which are configured to positively introduce external light, incidence of external light is restricted in this modification. The shielding unit is, for example, configured as a non-translucent cover that covers a region in front of the subject's eye E.

The holding units hold components of the visual function examination apparatus. "Holding" as used herein includes at least the meaning of any one or both of "supporting" and "storing (or housing)". The holding units include at least a first holding unit that holds the application optical system 10 and a second holding unit that holds the biological information detector 40. The holding units include, for example, a member(s) and/or a structure(s) for fixing the components to the housing.

The attachment unit has a configuration for the subject to wear the visual function examination apparatus. For example, the attachment unit has a configuration for attaching the visual function examination apparatus to the subject's head. Specifically, the attachment unit may include temples like eye glasses. The attachment unit may include a hat-like member or a belt-like member covering the subject's head. The attachment unit may include a cord-like member or a belt-like member to be hung on the subject's neck. The attachment unit may include a member that can be fixed to the subject's shoulder.

According to the configuration of the present modification, the visual function examination can be performed with the subject wearing part of or the whole of the visual function examination apparatus. With this, in the case of performing a visual field examination or the like in which the time required for the examination is relatively long, it is possible to perform the examination in a natural posture as compared to the conventional usage mode in which the examination is performed by looking into the fixedly installed apparatus. Also, it is easy to change the posture.

Furthermore, since the examination can be performed in a state where the field of view of the subject's eye E is shielded, there is no need to prepare a dark room. Further, it is unnecessary to shield the eye on the side opposite to the subject's eye E with the gauze or the eyepatch. Further, it is possible to reduce the size of the apparatus.

Fourth Embodiment

A system that includes a plurality of visual function examination apparatuses according to any of the above embodiments or any of the above modifications will be described. The visual function examination system according to the present embodiment includes a computer capable of data communication with the plurality of visual function examination apparatuses. The visual function examination apparatuses are used in medical institutions or outside medical institutions.

When used in a medical institution, the visual function examination apparatus is used in, for example, an examination room, a waiting room, an inpatients' ward, or the like. Further, the computer is installed in a medical institution or installed in a facility where the system service is provided (service center). The visual function examination apparatus and the computer communicate via a network system (LAN) built in the medical institution. Alternatively, the visual function examination apparatus and the computer transmit and receive data to and from each other with direct wired communication or wireless communication (for example, short-range wireless communication). When the computer is installed outside the medical institution (for example, when installed in the service center), an internal network in the medical institution and a wide area network (the Internet, a dedicated line, etc.) are interposed between the visual function examination apparatus and the computer. Incidentally, the medical institutions include not only hospitals, but also medical examination centers, screening centers, and the like.

When used outside a medical institution, the visual function examination apparatus is used, for example, at the subject's home, at an elderly welfare facility, at a drugstore, or the like. Also, a wide area network (and a medical institution internal network) is interposed between the visual function examination apparatus and the computer.

The visual function examination system described below can be applied to any of the above-described system modes. In addition, the following configurations can be applied to any system mode other than the above.

Figure 20:
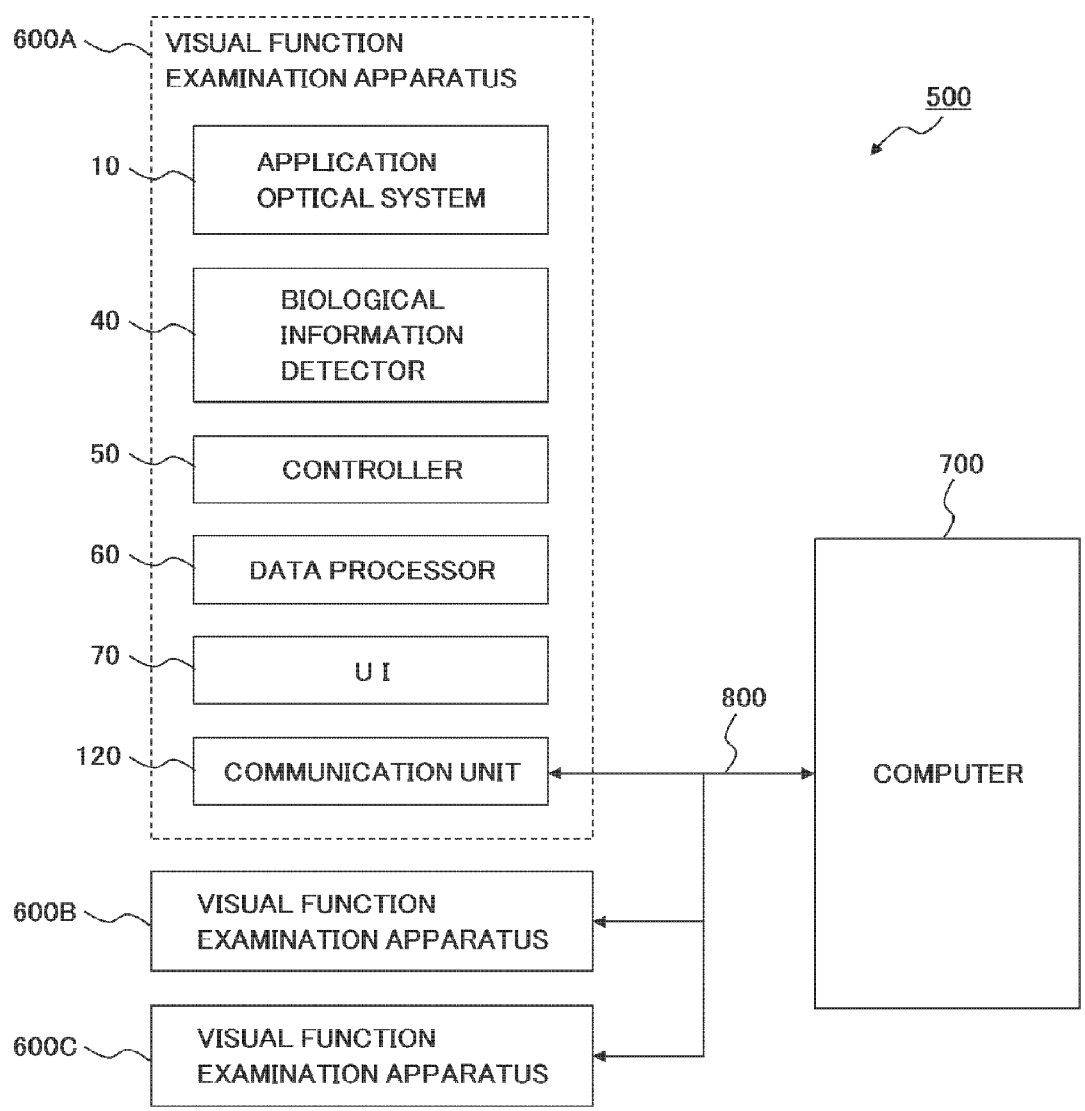
FIG. 20 is a schematic diagram illustrating an example of the configuration of a visual function examination system according to an embodiment.

An example of the configuration of the visual function examination system is shown in FIG. 20. The visual function examination system 500 includes a plurality of visual function examination apparatuses 600A, 600B, 600C, . . . and a computer 700. The number of the visual function examination apparatuses is arbitrary. Hereinafter, the plurality of visual function examination apparatuses 600A, 600B, 600C, . . . may be collectively referred to as "a plurality of visual function examination apparatuses 600". Further, an arbitrary one of the plurality of visual function examination apparatuses 600A, 600B, 600C, . . . may be referred to as "a visual function examination apparatus 600". The visual function examination apparatus 600 and the computer 700 are connected to each other via a communication line 800.

As in the above embodiments, the visual function examination apparatus 600 includes the application optical system 10, the biological information detector 40, the controller 50, the data processor 60, and the user interface 70. Furthermore, the visual function examination apparatus 600 in the present embodiment includes a communication unit 120. The communication unit 120 performs data communication through the communication line 800. Note that the visual function examination apparatus 600 may further include any of the image projection unit 80, the posture detector 90, the fixation determination unit 100, the eye movement monitoring unit 110, and the like.

The computer 700 includes, for example, a server, a computer terminal, or the like installed in a medical institution, or a server installed in a service center. The computer 700 may be a single device or a combination of two or more devices.

The computer 700 identifies the plurality of visual function examination apparatuses 600 by referring to the apparatus identification (apparatus ID) assigned to each of the visual function examination apparatuses 600 in advance. Thereby, the computer 700 can communicate with two or more visual function examination apparatuses 600 in parallel.

Figure 21:
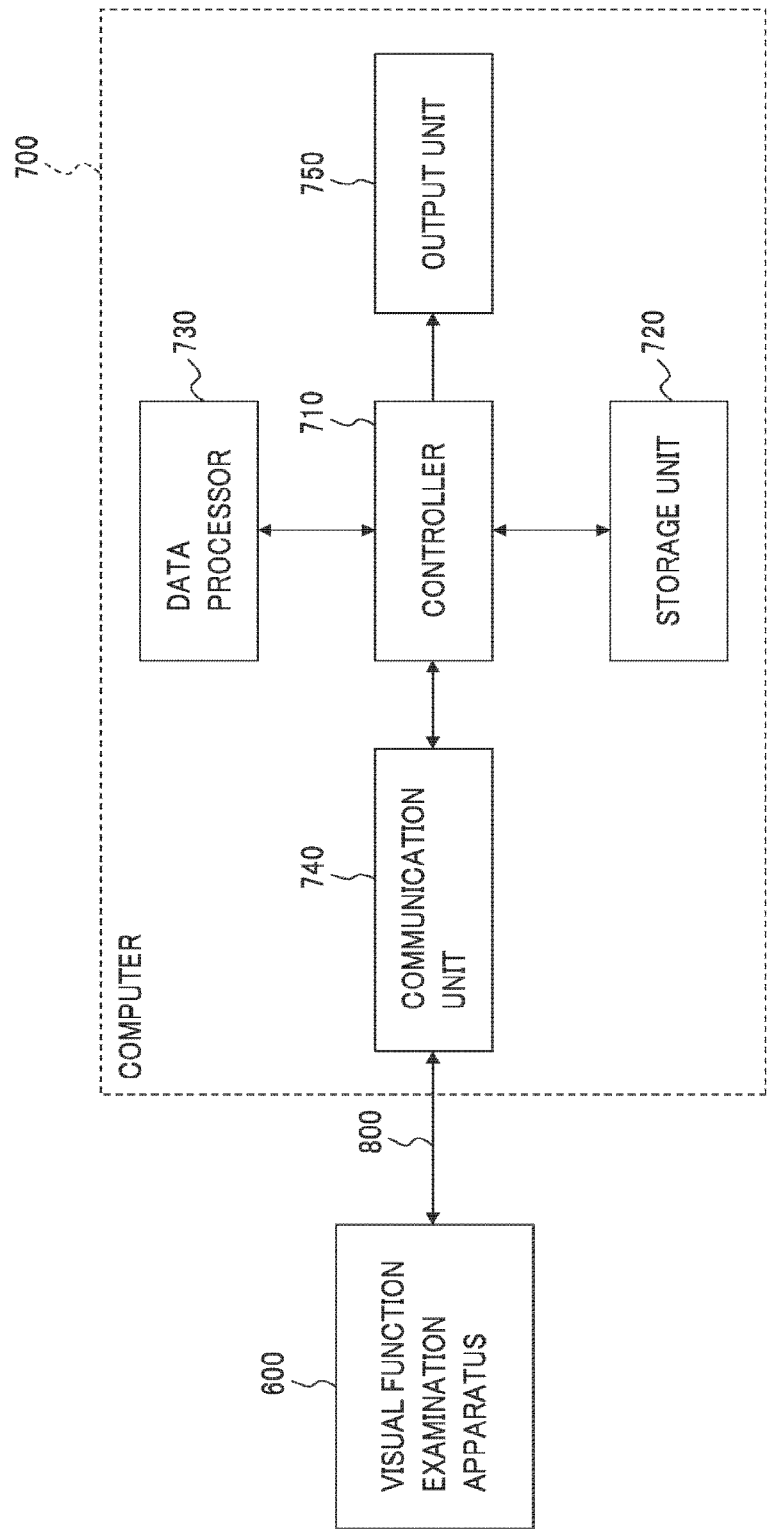
FIG. 21 is a schematic diagram illustrating an example of the configuration of the visual function examination system according to the embodiment.

An example of the configuration of the computer 700 is shown in FIG. 21. The computer 700 includes a controller 710, a storage unit 720, a data processor 730, a communication unit 740, and an output unit 750. Note that the computer 700 may include a display device, an operation device, and the like.

The controller 710 controls each part of the computer 700. The storage unit 720 stores various kinds of information. The data processor 730 executes various kinds of data processing. The communication unit 740 performs data communication through the communication line 800. The output unit 750 outputs information to an external device or to an information recording medium. The external device may be another computer, a tablet terminal, or the like. Output to the external device is performed through the communication line 800 or through another communication line. Examples of the information recording medium include a semiconductor memory, CD-ROM, printing paper, and the like. The output unit 750 has a configuration in accordance with the type of the information recording medium. In addition, the output unit 750 may include a display device.

In the storage unit 720, a storage area associated with each subject (account) is set. In each account, information related to the subject (patient ID, name, etc.), clinical information including the result of the visual function examination, and information on the fees (receipt information, system service usage fee, etc.) are recorded. The controller 710 performs the management of the account.

[Usage Mode]

Figure 22:
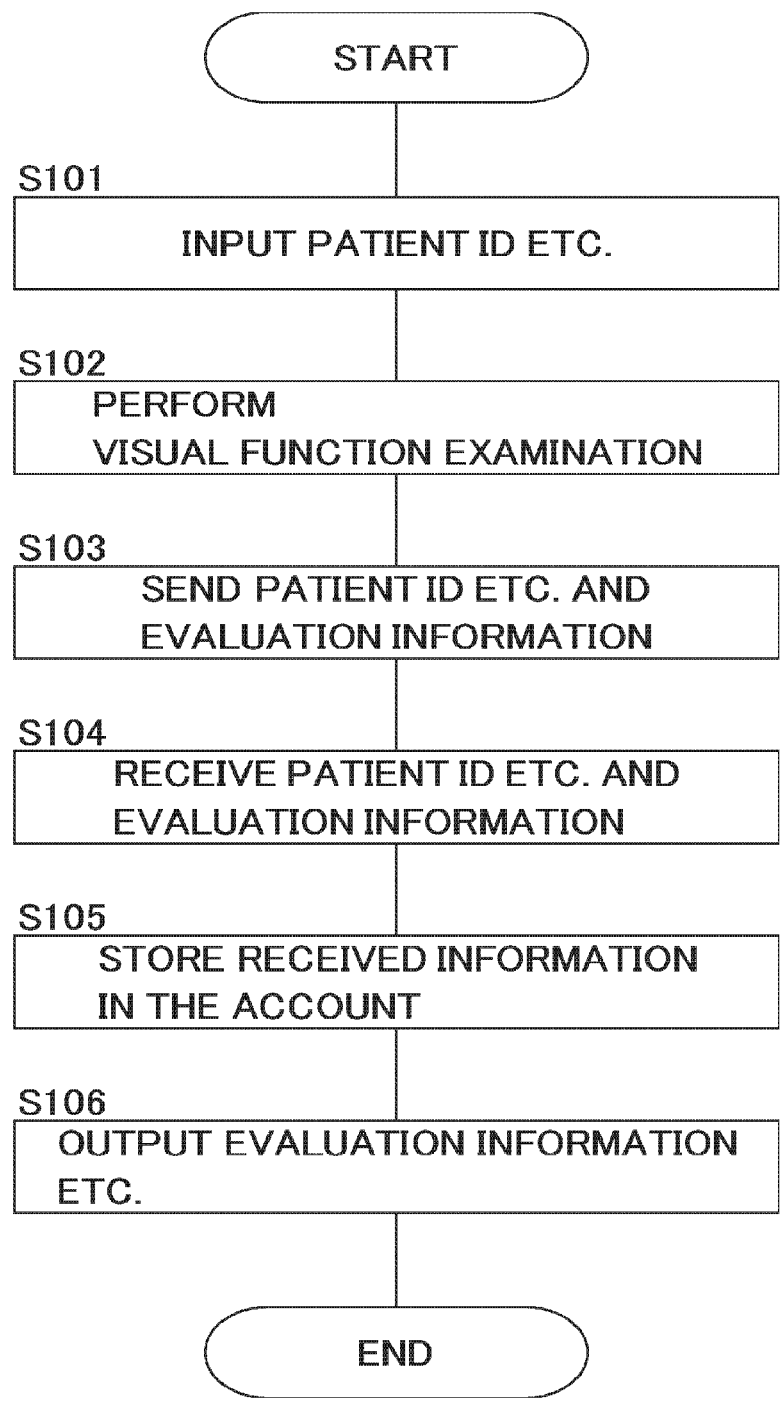
FIG. 22 is a flowchart illustrating an example of a usage mode of the visual function examination system according to the embodiment.

The usage mode of the visual function examination system 500 will be described. An example of the usage mode is shown in FIG. 22.

(S101: Input Patient ID Etc.)

First, the patient ID is input to the visual function examination apparatus 600 or to the computer 700. At this time, information indicating whether the subject's eye E is a left eye or a right eye (left eye information/right eye information) may be input. It is possible to provide a function of automatically recognizing whether the subject's eye E is a left eye or a right eye. The automatic recognition is performed, for example, based on the attachment aspect of the visual function examination apparatus 600. Alternatively, it is also possible to determine whether the subject's eye E is a left eye or a right eye based on the anterior segment image of the subject's eye E.

(S102: Perform Visual Function Examination)

The visual function examination of the subject's eye E is performed using the visual function examination apparatus 600. At this time, the examination may be performed for only one eye of the subject or for each of the both eyes. Alternatively, the binocular visual function examination may be performed.

The controller 50 of the visual function examination apparatus 600 associates the patient ID input in step S101 with the evaluation information acquired by the visual function examination. When the left eye information/right eye information is input, the controller 50 associates the patient ID and the left eye information/right eye information with the acquired evaluation information.

Further, the controller 50 can associate the examination type information indicating the type of the visual function examination with the acquired evaluation information. For example, when the binocular visual function examination is performed, the examination type information representing the binocular visual function examination is associated with the evaluation information. When two or more types of visual function examinations are performed, the controller 50 associates corresponding examination type information with each of the two or more pieces of evaluation information acquired.

(S103: Send Patient ID Etc. And Evaluation Information)

Under the control of the controller 50, the communication unit 120 sends the patient ID etc. and the evaluation information associated with each other in step S102 to the computer 700.

(S104: Receive Patient ID Etc. And Evaluation Information)

The communication unit 740 of the computer 700 receives the information sent from the visual function examination apparatus 600. The communication unit 740 sends the received patient ID etc. and the evaluation information to the controller 710.

(S105: Store Received Information in the Account)

The controller 710 receives the patient ID etc. and the evaluation information received by the communication unit 740. The controller 710 identifies the subject's account based on the patient ID. If the corresponding account does not exist, the controller 710 newly creates an account of the subject. The controller 710 stores the evaluation information in the identified account (or in the newly created account). Incidentally, it is possible to store examination date and time information representing the date and time of the visual function examination performed, together with the evaluation information etc.

(S106: Output Evaluation Information Etc.)

For example, upon receiving a predetermined output trigger, the controller 710 retrieves the evaluation information etc. stored in the account in step S105 and sends it to the output unit 750. The output unit 750 outputs the evaluation information etc. received from the controller 710, for example, in a mode corresponding to the output trigger.

For example, before outputting the above information, the data processor 730 can execute data processing based on the evaluation information. As a specific example, when a plurality of pieces of evaluation information corresponding to different examination dates and times are stored in the account, the data processor 730 can generate information in which these pieces of evaluation information are arranged in time series. The information is, for example, list information or graph information. The controller 710 sends the information generated by the data processor 730 to the output unit 750. The output unit 750 outputs the information.

[Effects]

The effects of the present embodiment will be described.

The visual function examination system 500 according to the present embodiment includes the plurality of visual function examination apparatuses 600 and the computer 700. Each visual function examination apparatus 600 may have the same configuration as any of the above embodiments or any of the above modifications. Further, each visual function examination apparatus 600 includes the communication unit 120 (a transmitter). The communication unit 120 transmits the evaluation information generated by the data processor 60 (evaluation information generator). The computer 700 is configured to be capable of data communication with each visual function examination apparatus 600. Further, the computer 700 includes the communication unit 740 (a receiver), the storage unit 720, and the output unit 750. The communication unit 740 receives the evaluation information transmitted from the communication unit 120 of the visual function examination apparatus 600. The storage unit 720 stores the evaluation information received by the communication unit 740. The output unit 750 outputs the evaluation information stored in the storage unit 720.

According to such a configuration, highly reliable evaluation information can be acquired in a short time by the visual function examination apparatus 600. Further, the evaluation information acquired by the plurality of visual function examination apparatuses 600 can be collectively managed. In addition, there is also a practical advantage such that the visual function examinations of a plurality of subjects can be performed in parallel.

Fifth Embodiment

A visual function examination system having a configuration different from that of the fourth embodiment will be described. In the fourth embodiment, each of the visual function examination apparatuses generates the evaluation information. In contrast, in the present embodiment, the computer generates the evaluation information based on the information acquired by each of the visual function examination apparatuses. This makes it possible to simplify the configuration of each visual function examination apparatus.

Figure 23:
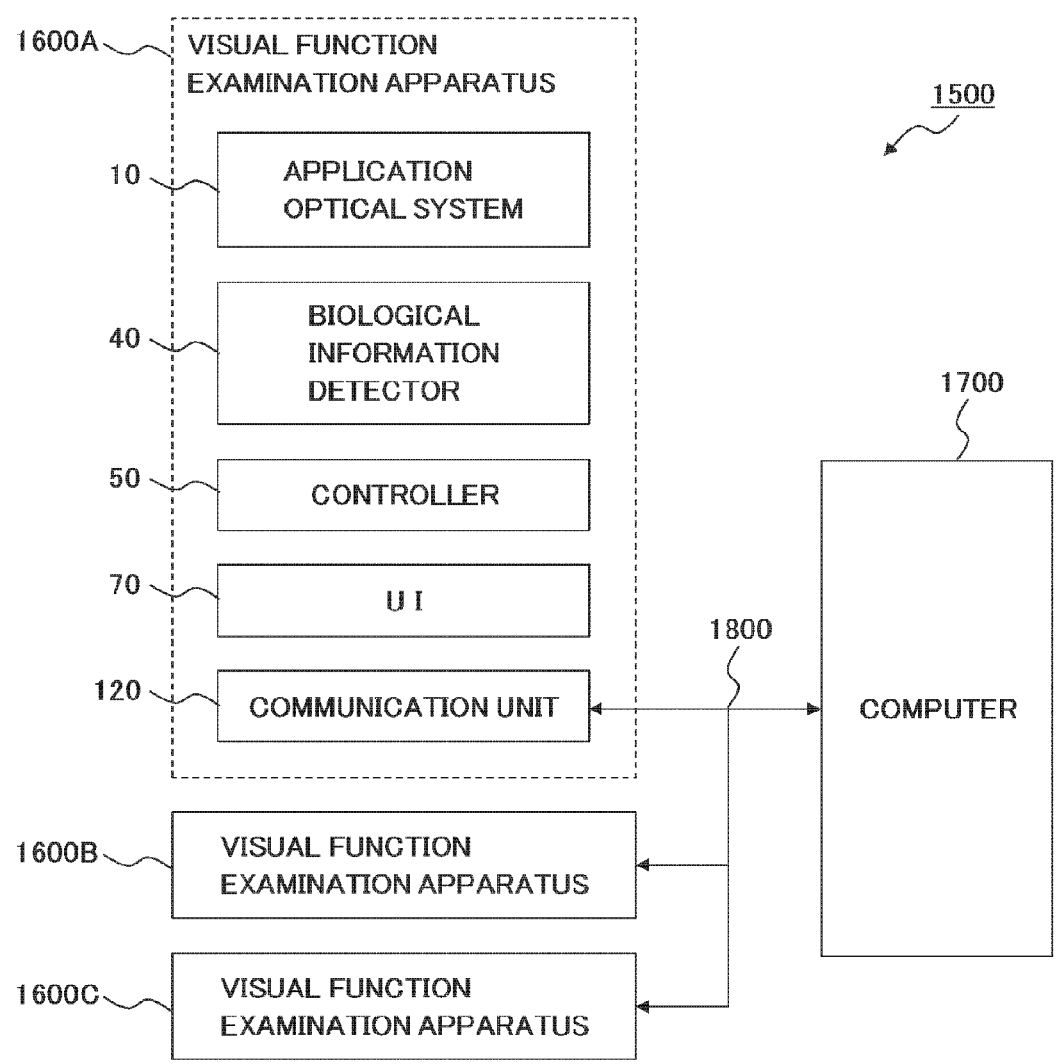
FIG. 23 is a schematic diagram illustrating an example of the configuration of the visual function examination system according to an embodiment.

FIG. 23 shows an example of the configuration of the visual function examination system according to the present embodiment. The visual function examination system 1500 includes a plurality of visual function examination apparatuses 1600A, 1600B, 1600C, . . . and a computer 1700. Hereinafter, the plurality of visual function examination apparatuses 1600A, 1600B, 1600C, . . . may be collectively referred to as "a plurality of visual function examination apparatuses 1600". Further, an any one of the plurality of visual function examination apparatuses 1600A, 1600B, 1600C, . . . may be referred to as "a visual function examination apparatus 1600". The visual function examination apparatus 1600 and the computer 1700 are connected to each other via a communication line 1800.

As in the above embodiments, the visual function examination apparatus 1600 includes the application optical system 10, the biological information detector 40, the controller 50, and the user interface 70. Note that the visual function examination apparatus 1600 according to the present embodiment need not have the function of generating evaluation information (that is, the function of evaluation information generator 61). However, the visual function examination apparatus 1600 may include this function. The visual function examination apparatus 1600 may include a data processor having other functions. Further, the visual function examination apparatus 1600 includes the communication unit 120 similar to that of the fourth embodiment. In addition, the visual function examination apparatus 1600 may further include any of the image projection unit 80, the posture detector 90, the fixation determination unit 100, the eye movement monitoring unit 110, and the like.

The computer 1700 includes, for example, a server installed in a medical institution, a computer terminal, or the like, or a server installed in a service center. The computer 1700 may be a single device or a combination of two or more devices.

Figure 24:
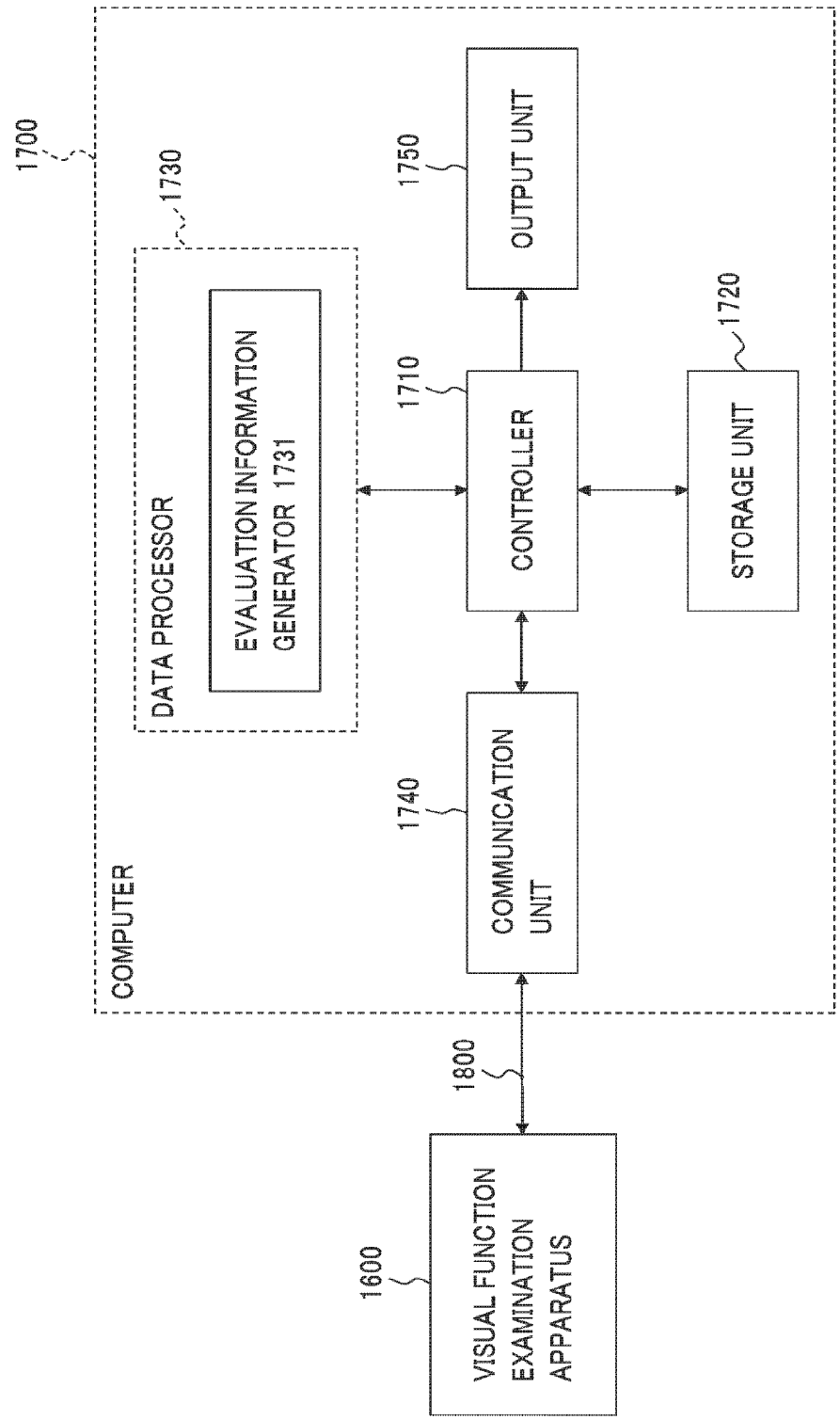
FIG. 24 is a schematic diagram illustrating an example of the configuration of the visual function examination system according to the embodiment.

An example of the configuration of the computer 1700 is shown in FIG. 24. The computer 1700 includes a controller 1710, a storage unit 1720, a data processor 1730, a communication unit 1740, and an output unit 1750. The data processor 1730 may include an evaluation information generator 1731. Note that the computer 1700 may include a display device, an operation device, and the like.

The controller 1710 controls each part of the computer 1700. The storage unit 1720 stores various kinds of information. The data processor 1730 executes various kinds of data processing. The evaluation information generator 1731 executes the same processing as the evaluation information generator 61 of the above embodiments. The communication unit 1740 performs data communication through the communication line 1800. The output unit 1750 outputs information to an external device or to an information recording medium.

In the storage unit 1720, as in the fourth embodiment, accounts of the respective subjects are set. The controller 1710 performs the management of the accounts.

[Usage Mode]

Figure 25:
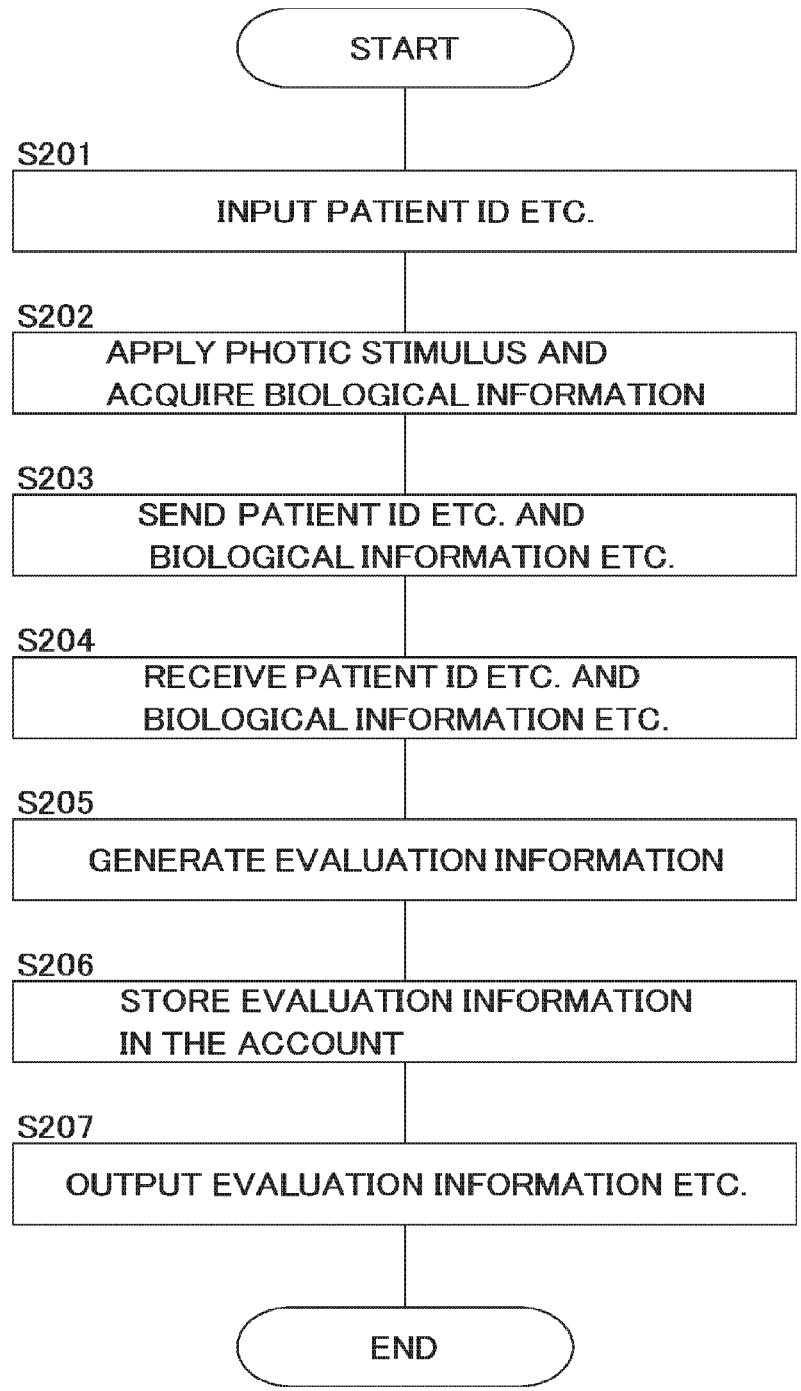
FIG. 25 is a flowchart illustrating an example of a usage mode of the visual function examination system according to the embodiment.

The usage mode of the visual function examination system 1500 will be described. An example of the usage mode is shown in FIG. 25.

(S201: Input Patient ID Etc.)

First, the patient ID is input to the visual function examination apparatus 1600 or to the computer 1700. At this time, left eye information/right eye information or the like may be input. The input of the patient ID and the left eye information/right eye information is performed in the same manner as in the fourth embodiment.

(S202: Apply Photic Stimulus and Acquire Biological Information)

The visual function examination of the subject's eye E using the visual function examination apparatus 1600 commences. In the visual function examination, biological information of the subject is acquired while applying a photic stimulus to the subject's eye E.

Further, the controller 50 adds information indicating the position to which the photic stimulus is applied (stimulation position information) to the biological information. The stimulation position information is generated, for example, based on the control contents of the optical scanner (the horizontal scanner 14 and the vertical controller 16). Alternatively, the stimulation position information may be generated based on order information of a plurality of stimulation points set in advance.

The controller 50 associates, with the biological information acquired, the patient ID input in step S201 and the stimulation position information indicating the application position of the photic stimulus when the biological information is acquired. At this time, the left eye information/right eye information and the examination type information may be further associated.

(S203: Send Patient ID Etc. and Biological Information Etc.)

In response to the control by the controller 50, the communication unit 120 sends the patient ID etc. and the biological information etc. associated with each other in step S202 to the computer 1700.

The relationship between the acquisition timing of the biological information and the transmission timing of the biological information etc. may be arbitrary. For example, it is possible to perform control so that the acquired biological information is transmitted to the computer 1700 collectively after the acquisition of the biological information has been completed. Alternatively, the acquired biological information may be divided into a plurality of pieces of information and transmitted to the computer 1700 after the acquisition of the biological information has been completed. In such cases, the visual function examination apparatus 1600 (the data processor 60) may include the function of detecting that the aforementioned "specific change" has occurred in the time course of the biological information and the function of going on to the examination of the next stimulation point in response to the detection of the specific change.

Alternatively, it is possible to perform control so as to perform transmission to the computer 1700 while acquiring biological information. In this case, the acquisition of biological information, the association of information, and the transmission of information are performed in parallel. In this case as well, the visual function examination apparatus 1600 may have the function of detecting the "specific change" and the function of going on to the examination of the next stimulation point in response to the detection of the specific change.

When the visual function examining apparatus 1600 is configured to execute parallel processing of acquiring biological information, associating information, and transmitting information in real time, the function of detecting the "specific change" may be installed in the computer 700. This processing is executed in real time by the data processor 1730 (for example, the evaluation information generator 1731). Further, the computer 700 notifies the visual function examination apparatus 1600 in real time of the fact that the specific change has been detected. Upon receiving this notification, the visual function examination apparatus 1600 goes on to the examination of the next stimulation point.
(S204: Receive Patient ID Etc. and Biological Information Etc.)

The communication unit 1740 of the computer 1700 receives the information transmitted from the visual function examination apparatus 1600. The communication unit 1740 sends the received patient ID etc. and the biological information etc. to the controller 1710.
(S205: Generate Evaluation Information)

The controller 1710 receives the patient ID etc. and the biological information etc. received by the communication unit 1740. The controller 1710 sends at least the biological information to the data processor 1730. The evaluation information generator 1731 generates evaluation information based on the biological information input.
(S206: Store Evaluation Information in the Account)

The controller 710 stores the evaluation information generated in step S205 in the subject's account. Here, the process of identifying an account is performed in the same manner as in the fourth embodiment. It is also possible to store information associated with the biological information and/or the information on the examination date and time together with the evaluation information etc.
(S207: Output Evaluation Information Etc.)

For example, upon receiving a predetermined output trigger, the controller 1710 retrieves the evaluation information etc. stored in the account in step S206 and sends it to the output unit 1750. The output unit 1750 outputs the evaluation information etc. received from the controller 1710.
[Effects]

The effects of the present embodiment will be described.

The visual function examination system 1500 according to the present embodiment includes the plurality of visual function examination apparatuses 1600 and the computer 1700. Each visual function examination apparatus 1600 may be configured similarly to the visual function examination apparatus 600 of the fourth embodiment, but the visual function examination apparatus 1600 need not include the function of generating evaluation information (the evaluation information generator 61). The communication unit 120 (the transmitter) transmits the detection result of the biological information acquired by the biological information detector 40. The computer 1700 is configured to be capable of data communication with each visual function examination apparatus 1600. Further, the computer 1700 includes the communication unit 1740 (the receiver), the evaluation information generator 1731, the storage unit 1720, and the output unit 1750. The communication unit 1740 receives the detection result of the biological information transmitted from the communication unit 120 of the visual function examination apparatus 1600. The evaluation information generator 1731 generates evaluation information on the visual function of the subject's eye E, based on the detection result of the biological information received by the communication unit 1740. The storage unit 1720 stores the evaluation information generated by the evaluation information generator 1731. The output unit 1750 outputs the evaluation information stored in the storage unit 1720.

According to such a configuration, highly reliable evaluation information can be acquired based on the biological information acquired by the visual function examination apparatus 1600. It is also possible to shorten the examination time. In addition, it is possible to collectively manage the evaluation information acquired using the plurality of visual function examination apparatuses 1600. Further, there is also a practical advantage such that the visual function examination of a plurality of subjects can be performed in parallel.

The configurations described above are mere examples for embodying or carrying out the present invention, and therefore susceptible to several modifications and variations (omission, substitution, addition, etc.), all coming within the scope of the invention. In addition, some of the above embodiments and modifications can be arbitrarily combined.

What is claimed is:

1. A visual function examination apparatus comprising:
    an application optical system including an optical scanner disposed in an optical path of laser light output from a laser light source and configured to apply the laser light that has travelled via the optical scanner to a retina of a subject's eye;
    a biological information detector including a sensor and memory configured to detect and record biological information representing a reaction of a subject to application of the laser light, the biological information detected by the biological information detector including at least one of an electroencephalogram, an electroretinogram, a magnetoencephalogram, an optical brain topogram, and a functional MRI image;
    processing circuitry configured to operate as an evaluation information generator configured to generate evaluation information on a visual function of the subject's eye based on the biological information detected by the biological information detector;
    a background image projector including a projection optical system configured to project a background image on the retina; and
    a controller configured to control the background image projector and the application optical system so as to perform projection of the background image and the application of the laser light in parallel.

2. The visual function examination apparatus of claim 1, wherein
    the biological information detector is configured to iteratively perform detection of the biological information, and
    the evaluation information generator is configured to generate the evaluation information based on time course of the biological information obtained through iterative detection performed by the biological information detector.

3. The visual function examination apparatus of claim 2, wherein:
    the controller is configured to control the application optical system so as to monotonically change application intensity of the laser light to one stimulation point of the retina while the iterative detection of the biological information is performed, and the evaluation information generator is configured to generate sensitivity information at the one stimulation point based on time course of the biological information according to the monotonic change of the application intensity of the laser light, and to generate, based on the sensitivity information generated for each of a plurality of stimulation points of the retina, distribution of the sensitivity information at the plurality of stimulation points as the evaluation information.

4. The visual function examination apparatus of claim 3, wherein the controller is configured to control the application optical system so as to apply the laser light to the one stimulation point under a first application condition, to apply the laser light to another site of the retina under a second application condition different from the first application condition, and to iteratively apply the laser light to the one stimulation point and the another site.

5. The visual function examination apparatus of claim 4, wherein the controller is configured to control the application optical system so as to, in response to generation of the sensitivity information at the one stimulation point, apply the laser light to a new stimulation point under the first application condition, to apply the laser light to a different site from the new stimulation point under the second application condition, and to iteratively apply the laser light to the new stimulation point and the different site from the new stimulation point.

6. The visual function examination apparatus of claim 3, further comprising an eye information memory configured to store information representing a structure of or a function of the subject's eye in advance, wherein
the controller comprises circuitry configured to perform as an initial intensity setting unit configured to set an initial value of the application intensity of the laser light based on the information stored in the eye information memory, and is configured to control the application optical system so as to commence applying the laser light to the one stimulation point from the initial value.

7. The visual function examination apparatus claim 3, further comprising an eye information memory configured to store information representing a structure of or a function of the subject's eye in advance, wherein
the controller comprises circuitry configured to perform as a stimulation point setting unit configured to set one or more stimulation points to which the laser light is to be applied based on the information stored in the eye information memory, and is configured to control the application optical system so as to apply the laser light to each of the one or more stimulation points set.

8. The visual function examination apparatus of claim 2, comprising a controller configured to control the application optical system so as to continuously change an application position of the laser light with respect to the retina while the iterative detection of the biological information is performed, wherein
the evaluation information generator is configured to generate information representing a range of visual field of the subject's eye as the evaluation information based on time course of the biological information according to continuous change of the application position of the laser light.

9. The visual function examination apparatus of claim 8, further comprising an eye information memory configured to store information representing a structure of or a function of the subject's eye in advance, wherein
the controller comprises circuitry configured to perform as an initial position setting unit configured to set an initial position of application of the laser light based on the information stored in the eye information memory, and is configured to control the application optical system so as to commence applying the laser light to the retina from the initial position.

10. The visual function examination apparatus of claim 1, wherein
the application optical system is configured to be capable of applying the laser light to a retina of a left eye of and to a retina of a right eye of the subject's eye.

11. The visual function examination apparatus of claim 10, wherein
the application optical system is configured to be capable of applying laser light to the retina of the left eye and to the retina of the right eye in parallel, and
the evaluation information generator comprises a component extractor that analyzes the biological information detected by the biological information detector to extract first components of the biological information corresponding to a reaction to the retina of the left eye and second components of the biological information corresponding to a reaction to the retina of the right eye, and is configured to generate left eye evaluation information on visual function of the left eye based on the left eye components extracted, and to generate right eye evaluation information on visual function of the right eye based on the right eye components extracted.

12. The visual function examination apparatus of claim 10, wherein
the application optical system is configured to be capable of applying laser light to the retina of the left eye and to the retina of the right eye in parallel, and
the evaluation information generator is configured to generate the evaluation information on binocular visual function of the left eye and the right eye based on the biological information detected by the biological information detector.

13. The visual function examination apparatus of claim 1, comprising a posture detector configured to detect posture of the subject, wherein
the evaluation information generator is configured to generate the biological information based on the biological information detected by the biological information detector and a detection result of the posture obtained by the posture detector.

14. The visual function examination apparatus of claim 1, wherein
the biological information detector is configured to detect two or more different types of biological information, and
the evaluation information generator is configured to generate evaluation information on each of two or more sites of visual system including the subject's eye based on the two or more biological information detected.

15. The visual function examination apparatus of claim 1, comprising:
a fixation target projector including a projection optical system configured to project a fixation target onto the retina of the subject' eye; and
a fixation determination unit configured to determine a fixation state of the subject's eye on which the fixation target is being projected; wherein
the evaluation information generator is configured to generate the evaluation information based on the biological information detected by the biological information detector when the fixation state of the subject's eye is determined as appropriate.

16. The visual function examination apparatus of claim 15, wherein
the fixation target is formed by the laser light projected onto the retina by the application optical system.

17. The visual function examination apparatus of claim 1, comprising:
an eye movement monitoring circuitry configured to monitor eye movements of the subject's eye; and
a scan controller configured to control the optical scanner based on output from the eye movement monitoring circuitry.

18. The visual function examination apparatus of claim 1, comprising:
a shielding unit configured to shield field of view of the subject's eye;
a first holding unit configured to hold the application optical system;
a second holding unit configured to hold the biological information detector; and
an attachment unit integrally formed with the shielding unit, the first holding unit, and the second holding unit, and configured to be attachable to the subject.

19. A visual function examination system, comprising:
a plurality of visual function examination apparatuses of claim 1; and
a computer configured to be capable of data communication with each of the plurality of visual function examination apparatuses; wherein
each of the plurality of visual function examination apparatuses comprises a transmitter configured to send the evaluation information generated by the evaluation information generator, and
the computer comprises:
a receiver configured to receive the evaluation information sent by the transmitter,
a memory configured to store the evaluation information received by the receiver, and
output circuitry configured to output the evaluation information stored in the memory.

20. A visual function examination system, comprising:
a plurality of visual function examination apparatuses and a computer configured to be capable of data communication with each of the plurality of visual function examination apparatuses; wherein
each of the plurality of visual function examination apparatuses comprises:
an application optical system including an optical scanner disposed in an optical path of laser light output from a laser light source and is configured to apply laser light that has travelled via the optical scanner to a retina of a subject's eye,
a biological information detector including a sensor and memory configured to detect and record biological information representing a reaction of a subject to application of the laser light, the biological information detected by the biological information detector including at least one of an electroencephalogram, an electroretinogram, a magnetoencephalogram, an optical brain topogram, and a functional MRI image, and
a transmitter configured to send a detection result of the biological information obtained by the biological information detector,
a background image projector including a projection optical system configured to project a background image on the retina, and
a controller configured to control the background image projector and the application optical system so as to perform projection of the background image and the application of the laser light in parallel, and
the computer comprises:
a receiver configured to receive the detection result of the biological information sent by the transmitter,
processing circuitry configured to operate as an evaluation information generator configured to generate evaluation information on a visual function of the subject's eye based on the detection result of the biological information received by the receiver,
a memory configured to store the evaluation information generated by the evaluation information generator, and
output circuitry configured to output the evaluation information stored in the memory.

* * * * *